(12) United States Patent
Alon et al.

(10) Patent No.: US 10,151,642 B2
(45) Date of Patent: Dec. 11, 2018

(54) SYSTEM AND METHOD FOR PROVIDING MAGNETIC RESONANCE TEMPERATURE MEASUREMENT FOR RADIATIVE HEATING APPLICATIONS

(71) Applicant: NEW YORK UNIVERSITY, New York, NY (US)

(72) Inventors: Leeor Alon, New York, NY (US); Daniel K. Sodickson, Larchmont, NY (US); Assaf Tal, New York, NY (US); Christopher M. Collins, Elizabethtown, PA (US)

(73) Assignee: NEW YORK UNIVERSITY, New York, NY (US)

( * ) Notice: Subject to any disclaimer, the term of this patent is extended or adjusted under 35 U.S.C. 154(b) by 258 days.

(21) Appl. No.: 15/167,841

(22) Filed: May 27, 2016

(65) Prior Publication Data

US 2016/0273970 A1    Sep. 22, 2016

Related U.S. Application Data

(63) Continuation-in-part of application No. PCT/US2014/067638, filed on Nov. 26, 2014.
(Continued)

(51) Int. Cl.
*G01K 7/00* (2006.01)
*G01K 1/00* (2006.01)
(Continued)

(52) U.S. Cl.
CPC ............... *G01K 3/08* (2013.01); *A61B 5/015* (2013.01); *A61B 5/055* (2013.01); *G01K 7/36* (2013.01);
(Continued)

(58) Field of Classification Search
USPC .................................. 374/163, 120
See application file for complete search history.

(56) References Cited

U.S. PATENT DOCUMENTS 4,558,279 A * 12/1985 Ackerman .......... A61K 49/06
324/300
2001/0004075 A1    6/2001 Wroe et al.
(Continued)

OTHER PUBLICATIONS

International Search Report for International Application No. PCT/US2014/067638 dated Apr. 13, 2015.
(Continued)

*Primary Examiner* — Mirellys Jagan
(74) *Attorney, Agent, or Firm* — Hunton Andrews Kurth LLP

(57) ABSTRACT

Exemplary embodiments of an apparatus according to the present disclosure comprise a radiative heating system with a radiation source configured to generate radiation for absorption by an object. A magnetic resonance system is provided with one or more coils configured to transmit and receive radio frequency energy to and from the object. A processor is configured to determine at least one of a temperature of the object and a change in the temperature of the object, based on the radio frequency energy received. A magnetic field source can be configured to generate a magnetic field within the object, and the radio frequency of the energy can be selected for magnetic resonance interactions in the object, based on a strength of the magnetic field.

30 Claims, 16 Drawing Sheets

Related U.S. Application Data

(60) Provisional application No. 61/909,824, filed on Nov. 27, 2013, provisional application No. 61/909,878, filed on Nov. 27, 2013.

(51) Int. Cl.

| | |
|---|---|
| *G01K 3/08* | (2006.01) |
| *A61B 5/055* | (2006.01) |
| *A61B 5/01* | (2006.01) |
| *G01R 33/48* | (2006.01) |
| *G01K 7/36* | (2006.01) |
| *G01K 11/00* | (2006.01) |

(52) U.S. Cl.
CPC ........ *G01K 11/006* (2013.01); *G01R 33/4804* (2013.01)

(56) References Cited

U.S. PATENT DOCUMENTS

| | | | |
|---|---|---|---|
| 2002/0097049 A1* | 7/2002 | Goto ................... | G01R 33/443 324/307 |
| 2004/0014236 A1* | 1/2004 | Albo .................... | G01R 33/389 436/173 |
| 2005/0070787 A1 | 3/2005 | Zeijlemaker | |
| 2007/0216410 A1* | 9/2007 | Thelissen ........... | G01R 33/4804 324/315 |
| 2008/0228063 A1 | 9/2008 | Turner et al. | |
| 2009/0149735 A1 | 6/2009 | Fallone et al. | |
| 2009/0192383 A1* | 7/2009 | Pananakis .............. | A61B 5/015 600/411 |
| 2010/0026298 A1* | 2/2010 | Wald .................. | G01R 33/5616 324/309 |
| 2010/0329414 A1 | 12/2010 | Zhu et al. | |
| 2011/0050223 A1* | 3/2011 | Balcom ................ | G01R 33/305 324/307 |
| 2016/0192859 A1* | 7/2016 | Shirai .................. | A61B 5/0042 600/412 |
| 2017/0261573 A1* | 9/2017 | Nakamura ......... | G01R 33/3614 |

OTHER PUBLICATIONS

International Written Opinion for International Application No. PCT/US2014/067638 dated Apr. 13, 2015.

Rieke, V. & Butts Pauly, K. MR thermometry. Journal Magn. Reson. Imaging vol. 27 pp. 376-390 (2008).

Zhu, Y., et al., System and SAR characterization in parallel RF transmission. Magn Reson Med, vol. 67 pp. 1367-1378 (2012).

Collins, C.M. et al., Temperature adn SAR Calculations for a Human Head Within Volume and Surface Coils at 64 and 300 MHz JMRU, Colume, 19 pp. 650-656 (2004).

Pearce, K. L., et al. Water distribution and mobility in meat during the conversion of muscle . . . quality attributes-A review. Meat Science, vol. 89 pp. 111-124 (2011).

Jean-Louis Damez and Sylvie Clerjon, Quantifying and predicting meat . . . using electromagnetic waves: An overview. Meat Science, vol. 95 pp. 879-896 (2013).

Luca Venturi., NMR Study of Meat as Related to its Structural Organisation. Doctorate thesis. universita' di bologna 2007.

Meredith, Roger , "Engineers' Handbook of Industrial Microwave Heating," IET Power & Energy Series 25, pp. 1-369, Dec. 1, 1998.

\* cited by examiner

Figure 1A
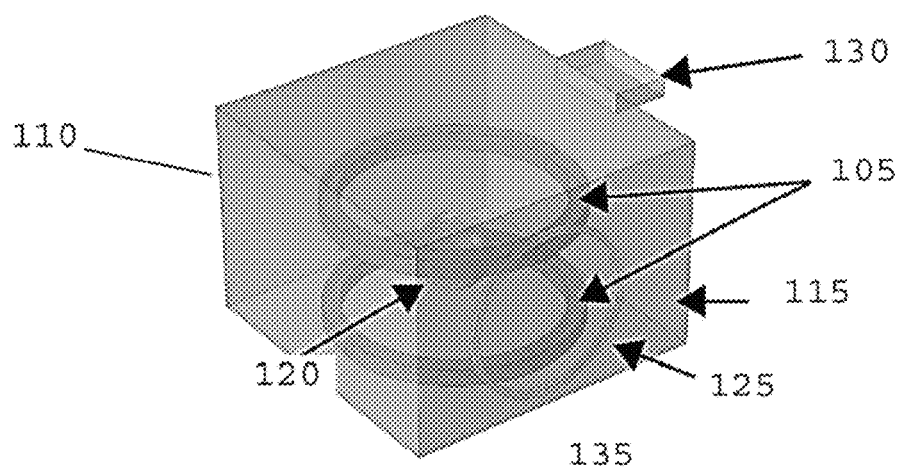
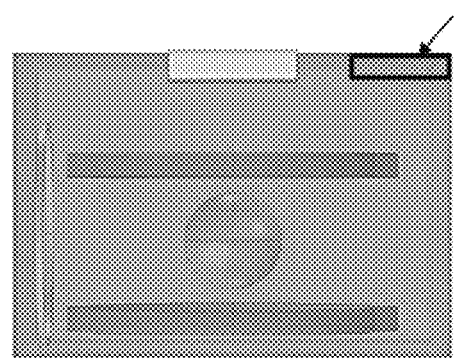
Figure 1B
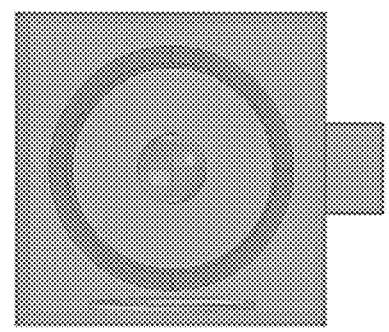
Figure 1C

Figure 3A
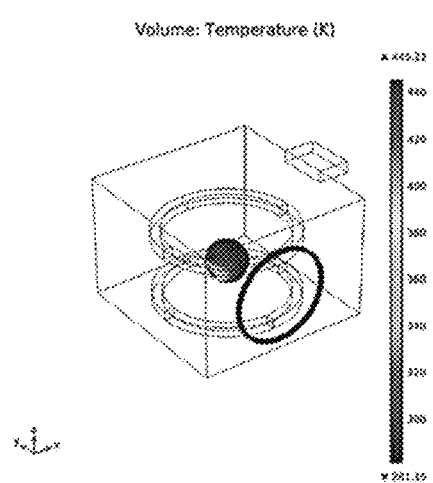
Figure 3B
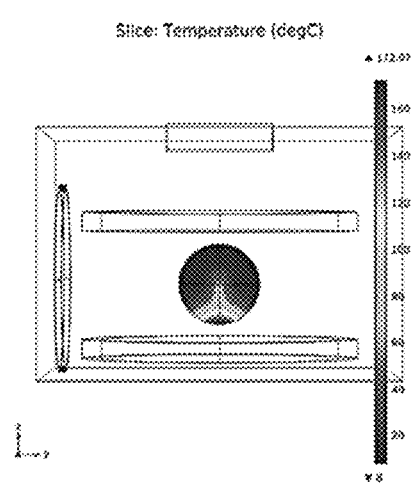
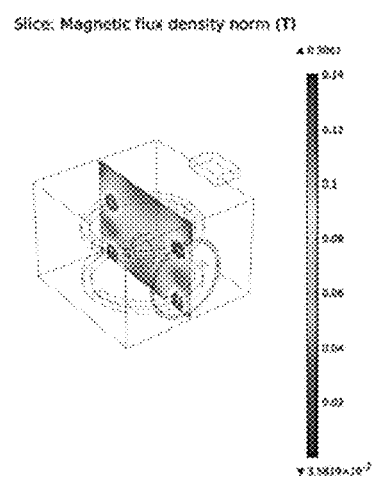
Figure 3C
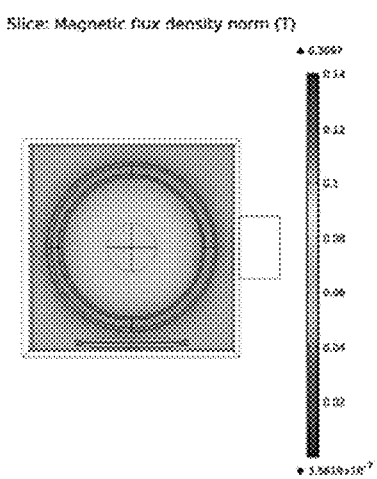
Figure 3D

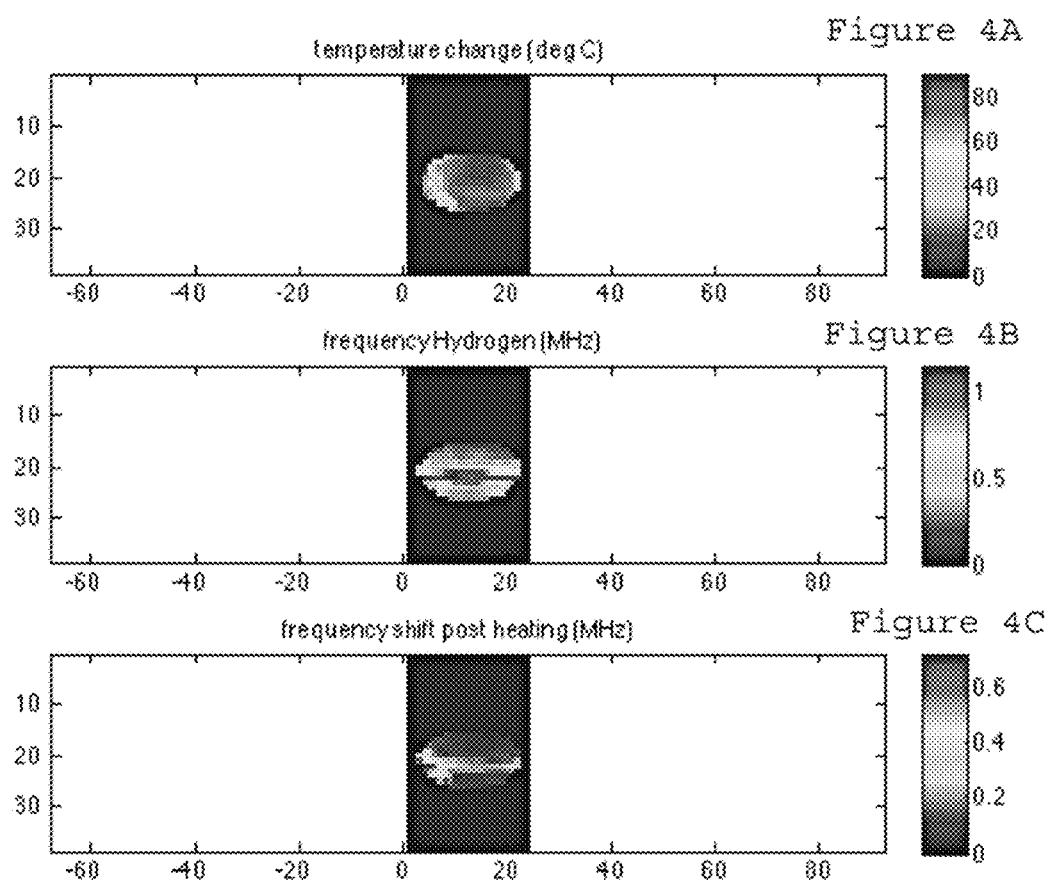

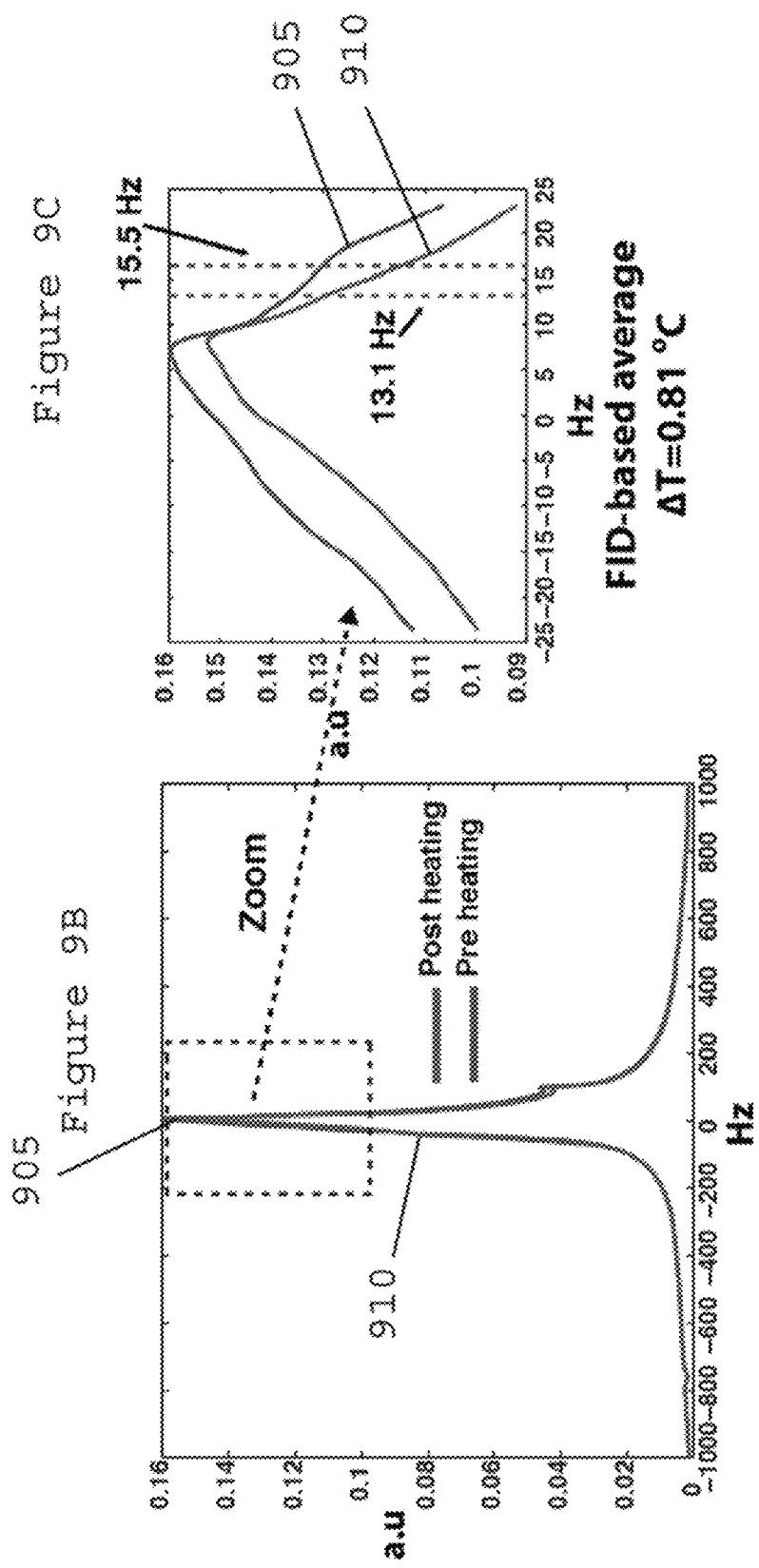

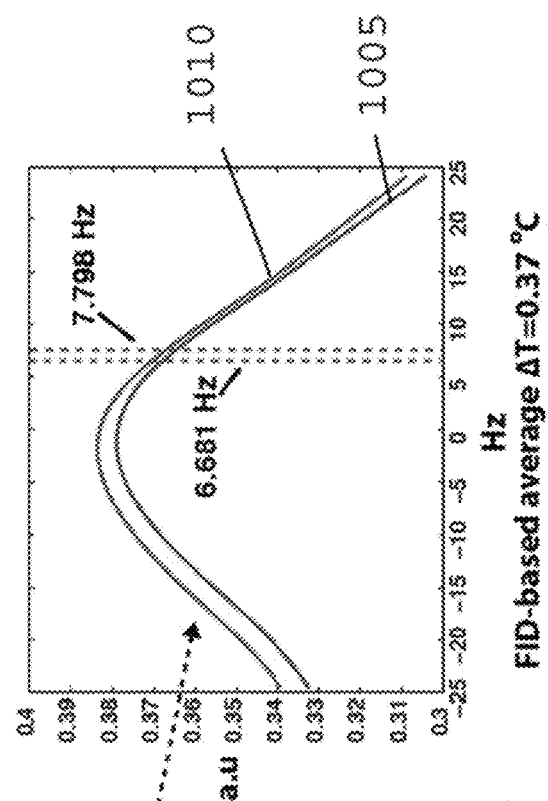
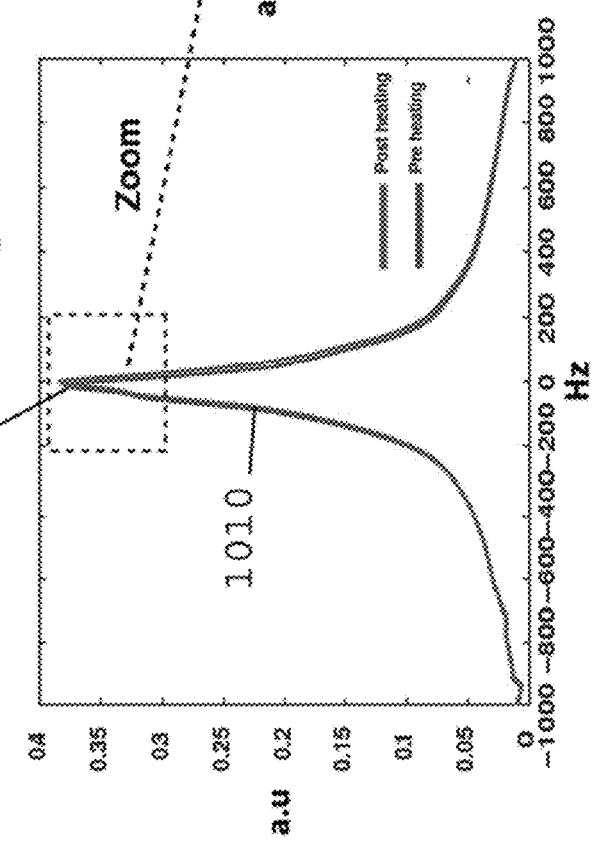
Figure 10B
Figure 10A

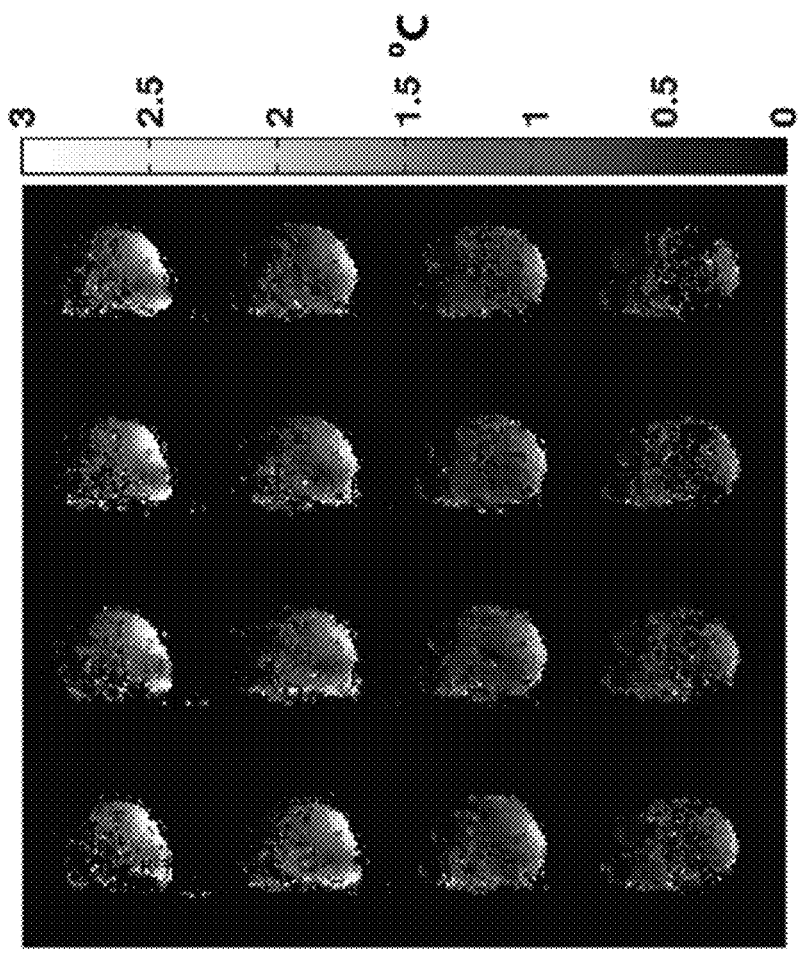

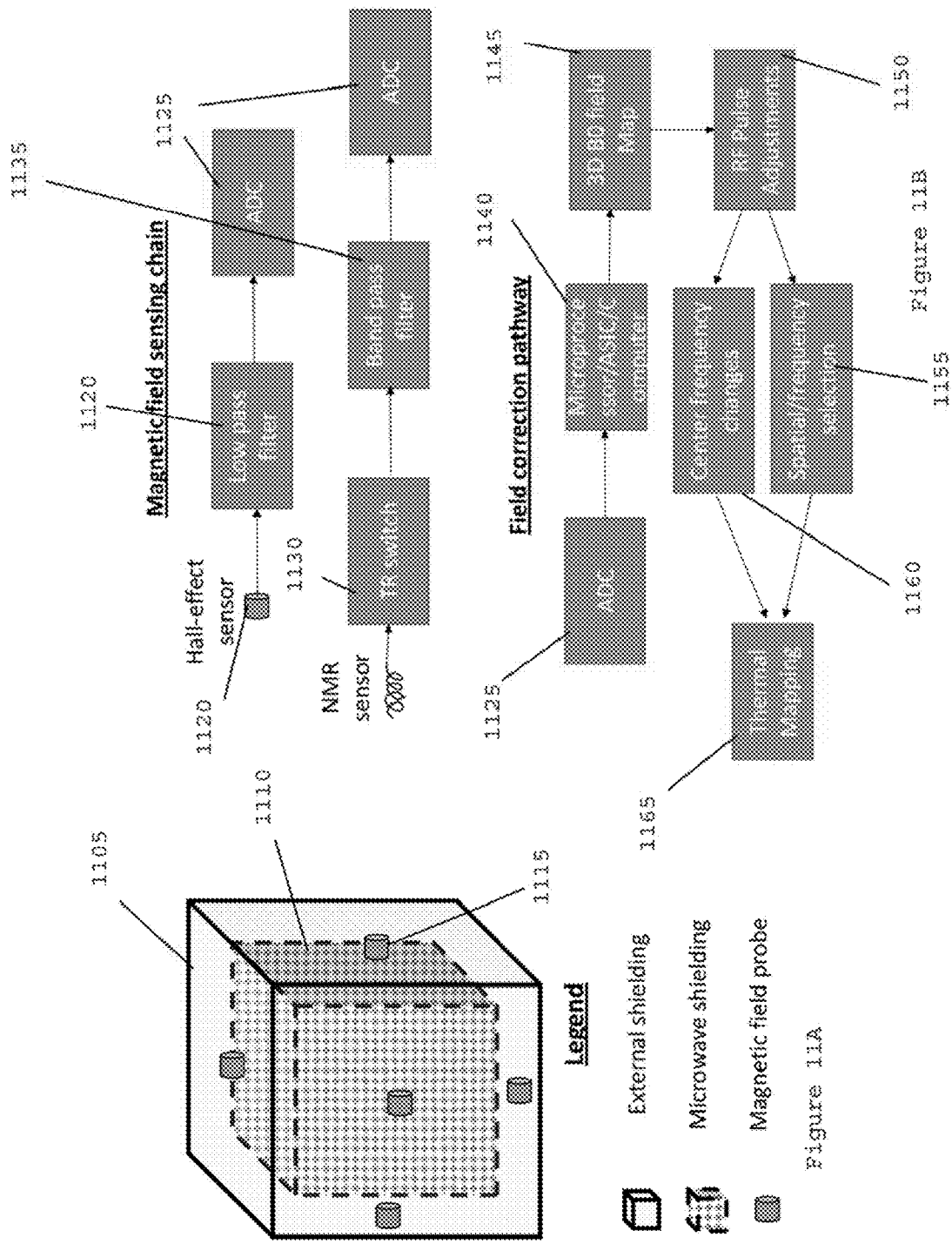

SYSTEM AND METHOD FOR PROVIDING
MAGNETIC RESONANCE TEMPERATURE
MEASUREMENT FOR RADIATIVE
HEATING APPLICATIONS

CROSS-REFERENCE TO RELATED
APPLICATION(S)

This application is a continuation-in-part application of International Patent Application No. PCT/US2014/067638 filed on Nov. 26, 2014, which relates to and claims priority from U.S. Patent Application No. 61/909,878, filed on Nov. 27, 2013, and 61/909,824, filed on Nov. 27, 2013 the entire disclosures of all of which are incorporated herein by reference.

FIELD OF THE DISCLOSURE

Exemplary embodiments of the present disclosure relate generally to temperature sensing, and specifically to an exemplary system, method and computer-accessible medium for facilitating a temperature measurement in microwave and other heating applications (e.g., radiative, conductive or convective). Further exemplary embodiments of the present disclosure relate to an exemplary system, method and computer-accessible medium systems and methods for facilitating a temperature measurement and/or temperature mapping in radiative heating environments, including, but not limited to, microwave ovens and other thermal and/or radiative heating systems.

BACKGROUND INFORMATION

Heating technologies can include both radiative, conductive and convective processes. Radiative heating processes can include, but are not limited to, heating by infrared ("IR") or thermal radiation and heating by absorption of microwave radiation. IR radiation can range in frequency from about 300 GHz in the far infrared up to about 400 THz in the near infrared. Microwave radiation can range in frequency from about 300 MHz in the meter wavelength range, corresponding generally to the upper frequency limit of the radio spectrum, to about 300 GHz in the millimeter wave range, corresponding generally to the lower frequency limit of the far infrared spectrum. Microwave oven technology, for example, can typically utilize electromagnetic ("EM") radiation, or waves with frequencies, at or in the range of about 915 MHz to about 2450 MHz (e.g., 2.45 GHz), which can be absorbed by many materials and can be used for heating foods and other substances. (See, e.g., Reference 1).

When utilizing microwave and other heating technologies (e.g., ovens), an object or body can be heated for a set time or duration, and direct temperature monitoring of the heated object itself may not be conducted. In some examples, a microwave or oven-compatible temperature probe can be inserted into an object for interior temperature measurements, but both microwave and thermal radiation processes can heat materials non-uniformly, and a single thermometer or probe measuring the temperature at a single point in space may not provide a suitable temperature measurement for all applications, particularly where there can be substantial temperature sensitivity. Monitoring of a global radio frequency ("RF") power deposition can be an aspect of patient safety in magnetic resonance ("MR") techniques, including magnetic resonance imagining ("MM"), and in other applications where patients, users, or other persons or bodies can be exposed to radio frequency radiation. For example, global RF power deposition can be estimated in phantom targets and subjects in vivo, for single and multiple transmit MM systems. (See, e.g., Reference 1). Generally, these RF power monitoring systems measure the forward (e.g., input) and reflected power, and calculate a net injected or deposited RF power into the patient, or other body, based on these factors.

In practice, however, losses can occur in one or more of the transmit chain electronics, coil structure, and radiated energy, such that estimates based on the forward power input may not represent the actual dose or RF energy absorbed. Other factors can also reduce the accuracy of the estimated amount of power that can be deposited within the target object, such as variable coupling of the target body to the RF coil.

Thus, there can be a need for an exemplary system, method and computer-accessible medium for providing magnetic resonance temperature measurement for heating applications, which can overcome at least some of the problems described herein above.

SUMMARY OF EXEMPLARY EMBODIMENTS

To that end, the exemplary system, method and computer-accessible medium, according to an exemplary embodiment of the present disclosure, can facilitate applications of MR techniques to temperature measurement and/or temperature mapping in heating environments, including, but not limited to, microwave, conductive and convective heating systems.

Exemplary embodiments of the present disclosure can be provided for applying exemplary MR techniques to RF power deposition, including bulk RF power deposition measurements with free induction decay acquisition. In some of these exemplary embodiments, a body can be exposed to RF energy, or RF radiation, to induce spin resonance in a magnetic field, and temperature changes in the body can be estimated or measured by acquiring free induction decay signals, and by determining the temperature change by comparing the signals.

The exemplary system, method and computer-accessible medium, according to an exemplary embodiment of the present disclosure can facilitate RF power deposition measurements with free induction decay acquisition, including frequency shift measurements related to target heating. According to at least some of these exemplary embodiments, images of the body can be generated with a magnetic resonance imaging system. In additional exemplary embodiments of the present disclosure, one or both of the RF energy exposure and the magnetic field strength, or magnitude, can be controlled based on the change in temperature, and/or based on an RF dose and/or specific absorption rate based on the change in temperature.

An exemplary embodiment of the present disclosure can be, for example, an apparatus, which can include a radiative heating arrangement including a radiation source which can be configured to generate a radiation(s) for absorption by an object(s), a magnetic resonance (MR) arrangement including an arrangement(s) which can be configured to transmit and receive radio frequency (RF) energy to and from the object(s), and a computer arrangement which can be configured to determine information regarding the object(s) based on the RF energy received from the object(s). The RF frequency energy received from the object(s) can include an MR spectrum. The information can be determined based on a first moment of the MR spectrum. The information can include a temperature(s) of the object(s) or a change(s) in the temperature(s) of the object(s)

In some exemplary embodiments of the present disclosure, an image(s) of the object(s) can be generated based on the received RF energy. The image(s) can represent an interior of the object(s). The image(s) can include a temperature map of the interior of the object(s). The MR apparatus can be provided within the housing. The MR apparatus can include a field source configured to generate a magnetic field within the object(s). The RF energy transmitted to the object(s) can have a characteristic(s) for facilitating a MR therein based on the magnetic field. A controller can be configured to control the radiative heating arrangement based on the information. The controller can be configured to increase or decrease a power output or a duty cycle of the radiative heating arrangement based on the information.

In some exemplary embodiments of the present disclosure, the radiative heating arrangement can include a microwave generator configured to generate a microwave radiation for absorption by the object(s). A structure can define a cavity configured to hold the object(s), which can be a Faraday cage. The radiation(s) can be microwave radiation, thermal radiation or infrared radiation. A field source can include a pair of Helmholtz coils disposed about a cavity configured to hold the object(s), where the pair of Helmholtz coils can be configured to generate a magnetic field inside the object(s) within the cavity. A gradient coil(s) can be configured for special localization of the RF energy received from the object(s).

A further exemplary embodiment can include an exemplary system, method and computer accessible medium for determining a temperature change(s) in structure(s), which can include, for example, receiving information related to first and second free induction decay signals provided from the structure(s), where each of the first and second free induction signals can be based on a radio frequency (RF) energy transmitted to the structure(s), determining the temperature change(s) in the structure(s) based on the information. Further information related to first and second RF frequency spectra that characterize the first and second free induction decay signals, respectively, can be generated. A respective first moment of each of the first and second RF frequency spectra can also be generated. The temperature change can be determined based on a difference between the first moment of the first RF spectrum and the first moment of the second RF spectrum. The temperature change can be determined by scaling the temperature change substantially linearly by a difference between the first moment of the first RF spectra and the second moment of the second RF spectra.

In some exemplary embodiments of the present disclosure, The temperature change(s) can be determined by dividing the difference by a proton shift coefficient and a Larmor frequency characteristic of the structure(s) in a magnetic field. A magnitude of the magnetic field or a magnitude of the RF energy to which the structure(s) is exposed can be controlled based on the temperature change(s). A thermal dose(s) applied to the structure(s) based on the temperature change(s) can be determined. A magnitude of a magnetic field or a magnitude of the RF energy to which the structure(s) can be exposed can be controlled based on the thermal dose; the thermal dose can include a specific absorption rate (SAR) of the RF energy by the structure(s).

In some exemplary embodiments of the present disclosure, further RF energy can be received from the structure(s) that can be based on the RF energy, and an image of an interior of the structure(s) can be generated based on the further RF energy. The image can include a map of the temperature change(s) in an interior of the structure(s). A specific absorption rate (SAR) of the RF energy can be estimated based on the temperature change(s). A magnitude of a magnetic field to which the structure(s) can be exposed can be controlled based on the SAR. A magnitude of the RF energy can be controlled based on the SAR.

In some exemplary embodiments of the present disclosure, exposure of the structure(s) to the RF energy can be terminated based on the SAR. The SAR can be estimated by scaling the temperature change(s) by a specific heat of the structure(s) divided by an exposure time of the structure(s) to the RF energy. The image can include a map of the specific absorption rate in an interior of the structure(s). The exposure of the structure(s) to the RF energy in a magnetic field can be controlled, and a frequency of the RF energy for resonant spin interactions with the structure(s) can be selected based on a magnitude of the magnetic field.

These and other objects, features and advantages of the present disclosure will become apparent upon reading the following detailed description of exemplary embodiments of the present disclosure, when taken in conjunction with the accompanying exemplary drawings and appended claims.

BRIEF DESCRIPTION OF THE DRAWINGS

The foregoing and other objects of the present disclosure will be apparent upon consideration of the following detailed description, taken in conjunction with the accompanying exemplary drawings and numbered paragraphs showing illustrative embodiments of the present disclosure, in which:

FIG. 1A is a perspective view of a representative heating system with a magnetic resonance ("MR") thermal sensing system according to an exemplary embodiment of the present disclosure;

FIG. 1B is a side view of the representative heating system and MR thermal sensing system according to an exemplary embodiment of the present disclosure;

FIG. 1C is a top view of the representative heating system and MR thermal sensing system according to an exemplary embodiment of the present disclosure;

FIG. 3A is a perspective view illustrating a temperature change in a representative volume of an object, generated by a radiative heating apparatus and imaged by an MR system, according to an exemplary embodiment of the present disclosure;

FIG. 3B is a side view illustrating the temperature change in a representative slice of the exemplary object, generated by a radiative heating apparatus and imaged by an MR system, according to an exemplary embodiment of the present disclosure;

FIG. 3C is a top view illustrating magnetic flux density in a representative vertical slice taken across a cavity within a heating apparatus according to an exemplary embodiment of the present disclosure;

FIG. 3D is top view illustrating magnetic flux density in a representative horizontal slice taken across the cavity within a heating apparatus according to an exemplary embodiment of the present disclosure;

FIG. 4A is an image of the temperature change in a representative slice of a sample in a heating apparatus with an MR system according to an exemplary embodiment of the present disclosure;

FIG. 4B is an image of precession frequency in the representative slice of the sample in a heating apparatus with an MR system according to an exemplary embodiment of the present disclosure;

FIG. 4C is an image of precession frequency shift in the representative slice of the sample in a heating apparatus with an MR system according to an exemplary embodiment of the present disclosure;

FIG. 9B is a frequency plot of free induction decay ("FID") acquisition signals or spectra, illustrating the frequency shift due to RF heating of the phantom, according to an exemplary embodiment of the present disclosure;

FIG. 9C is an enlarged view of the frequency plot shown in FIG. 9B, illustrating the peak region, according to an exemplary embodiment of the present disclosure;

FIG. 10A is a frequency plot of FID acquisition signals or spectra, illustrating the frequency shift due to RF heating of the in vivo subject, according to an exemplary embodiment of the present disclosure;

FIG. 10B is an enlarged view of the frequency plot in FIG. 10A, showing the peak region according to an exemplary embodiment of the present disclosure;

FIG. 10C is a series of thermometry images of the exemplary in vivo subject according to an exemplary embodiment of the present disclosure;

FIG. 11A is a diagram of an exemplary structure/design of inner and outer shields used in or with the exemplary system/method according to an exemplary embodiment of the present disclosure;

FIG. 11B is an exemplary schematic/flow diagram of the exemplary system/method according to an exemplary embodiment of the present disclosure.

Figure 1D:
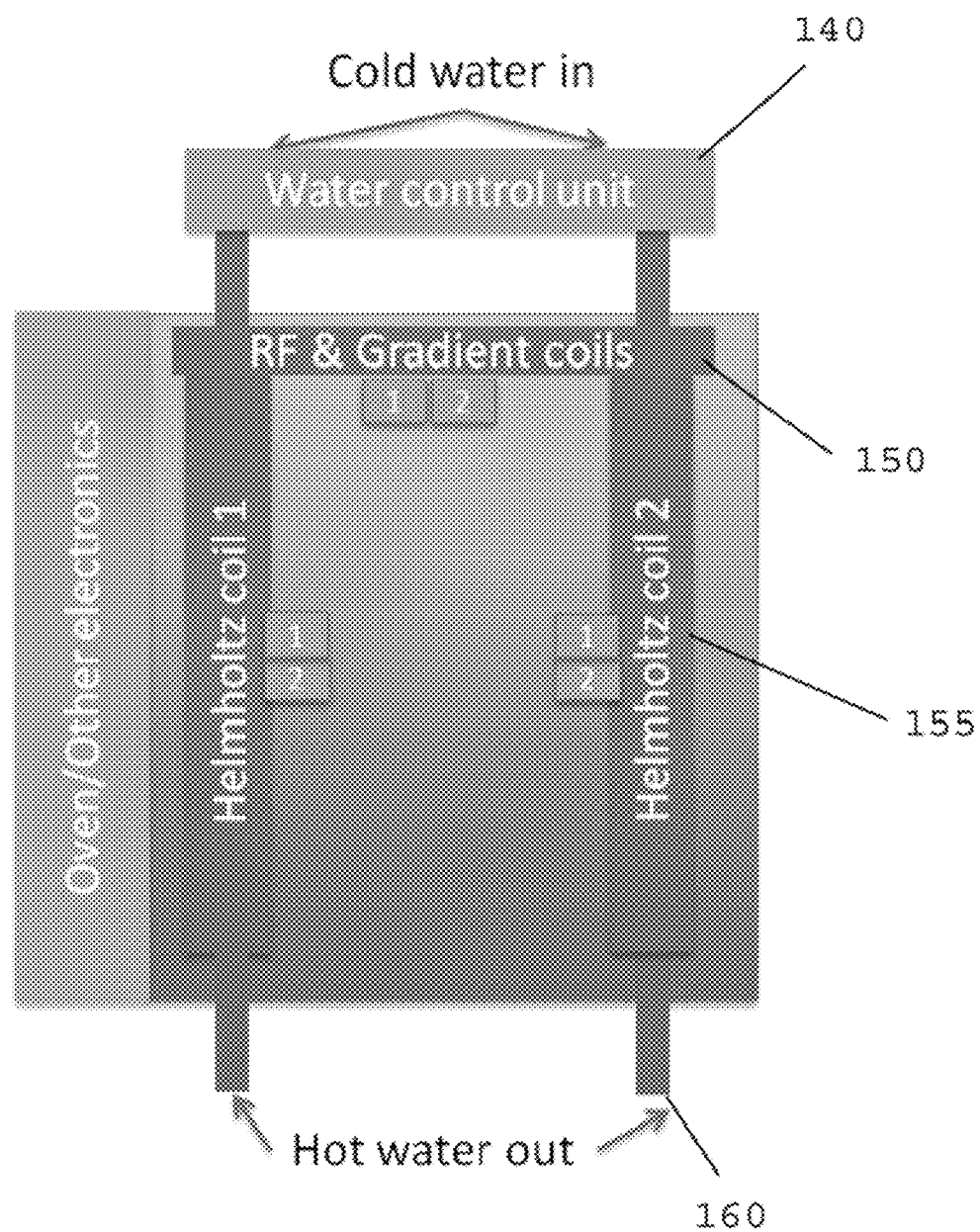
FIG. 1D is an exemplary diagram of an exemplary cooling system according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures or provided in the appended claims.

DETAILED DESCRIPTION OF EXEMPLARY EMBODIMENTS

When utilizing heating technologies, an object or a body can be heated for a set time or duration, and temperature monitoring can be conducted. In some examples, a microwave-compatible temperature probe can be inserted into the object being heated. However, the heating of materials/objects can occur non-uniformly, and therefore, a single thermometer measuring the temperature at a single point in space may not be a good method for temperature measurement. According to an exemplary embodiment of the present disclosure, a non-invasive radiative and microwave-compatible, or other heating compatible, system, method and computer-accessible medium can be provided, for monitoring the temperature change during heating based on MR techniques, for example, MM.

Magnetic resonance thermometry ("MRT") mapping can be used to measure the temperature changes in phantoms, in vivo bodies and other objects, for example, where heating can result from the deposition of energy (e.g., radiative) in dielectric materials. (See, e.g., Reference 2). According to an exemplary embodiment of the present disclosure, a Helmholtz coil, and/or another magnetic field generator, can be inserted inside a heating apparatus, and driven with a direct current ("DC") supply. The current applied to the coil or field generator can generate a magnetic field distributed inside the microwave or radiative heating apparatus, which can be substantially decoupled from the radiating heating field. For example an infrared ("IR") field or an alternating RF field at or in the range of about 915 MHz to about 2450 MHz in frequency can be used.

When a dielectric object, or body, can be exposed to the magnetic field, atoms in the object, or the magnetic moments or spins thereof, can precess at a frequency that can be proportional to the strength of the magnetic field. (See, e.g., Reference 2). The temperature change induced by microwave and/or another heating apparatus can alter the precession frequency of these atoms, as the electron shielding effect changes the effective magnetic field that these atoms "see" or experience. (See, i.d.).

In some exemplary embodiments of the present disclosure, for example as illustrated in FIGS. 1A-1C, a Helmholtz coil 105 can be inserted into the housing 110 of a microwave oven or other radiative heating apparatus. The housing 110 can be formed of, and/or provided substantially as, a Faraday cage or Faraday "box," or can otherwise provide electromagnetic shielding, for example, with a substantially continuous metal or conductive housing or liner configured to shield the interior of the heating apparatus from external electric fields and electromagnetic radiation, and to reduce leakage or electromagnetic radiation to the outside (e.g., a copper housing 115). Depending on the radiation frequency of interest, the Faraday structure can also be discontinuous, with discontinuities sized to prevent or discourage passage of radiation therethrough, for example, with a plurality of holes or apertures sized substantially below the characteristic wavelength of radiation having the frequency of interest.

The top and bottom coils 105 (e.g., Helmholtz or other field-generating structures) can create a static magnetic field inside the heating apparatus, including within any tissue-like object, body, or sample, for example a food item or another object or material represented by a sphere (e.g., a dielectric sample 120). An MR coil 125 can also be provided, and tuned to a resonant frequency which can depend on the strength of the magnetic field generated by the Helmholtz coils, or other field generator. The MR coil can typically be connected to an RF amplifier when exciting the spins in the object, and to a receive chain when measuring signals from the object. The MR coil 125 can be used for thermal sensing via MR imaging techniques, as described herein. It can also be possible to include gradient coils within the apparatus, so that improved spatial localization of the MR signal can be obtained.

As shown in FIG. 1A, the heating apparatus can include a radiation generator and/or a radiation source 130 such as, for example, a microwave waveguide in combination with a klystron or magnetron system, or an infrared radiation generator such as a heated coil or other thermal radiation or thermal energy source. The radiation source can be configured to generate radiation for an absorption by an object within the housing 110 of the heating apparatus, for example, a food item inside an oven area defined within the housing, or an another material disposed within a cavity defined inside the housing. Radiative heating can be generated by a direct absorption of a radiative, conductive or convective energy in the body to be heated.

In the exemplary embodiments shown in FIGS. 1A-1C, the microwave or other heating apparatuses can be shielded from external RF, IR, and microwave EM radiation, or other sources of heating, in order to substantially minimize interference from electromagnetic radiation or waves from outside the housing, which can alter or affect the MR measurements described herein. The shielding can also contain the radiation within the heating apparatus, and can prevent and/or reduce a deposition of the microwave energy on or into subjects and other objects disposed outside the microwave, or other radiative heating apparatus. As shown in FIG. 1B, a display 135 can be used to display information about the exemplary system (e.g., temperature of object 120).

The exemplary system, method and computer-accessible medium, according to an exemplary embodiment of the present disclosures can be used in apparatuses that can generate heat by means of radiation, convection and conduction. In exemplary cases where the MRI system cannot be shielded from the radiation source (e.g., as in conventional ovens), or when the heated object can heat the magnet electronics, a water-cooling system can be introduced to the magnet system, where the transport of water by means of forced convection can dissipate heat from the magnet system. (See e.g., FIG. 1D). This can facilitate utilization of nuclear magnetic resonance ("NMR")/MRI technology at high ambient operating temperatures such as in ovens. For example, cold water can enter into a water control unit 140, and can be used to cool RF and gradient coils 150, and Helmholtz coils 155. The resulting hot water can exit through pipes 160.

The flow of the water into the exemplary system can be controlled using a sensing circuit where a microcontroller can be connected to a magnetic field hall-effect and temperature sensors located on the RF, gradient and magnet coils. Information provided by these sensors can control a water control unit that can regulate the flow and temperature of the water flowing into the MR system by means of a feedback mechanism. In case the temperature increases above a certain threshold, shutdown of the magnet system can take place.

Figure 2:
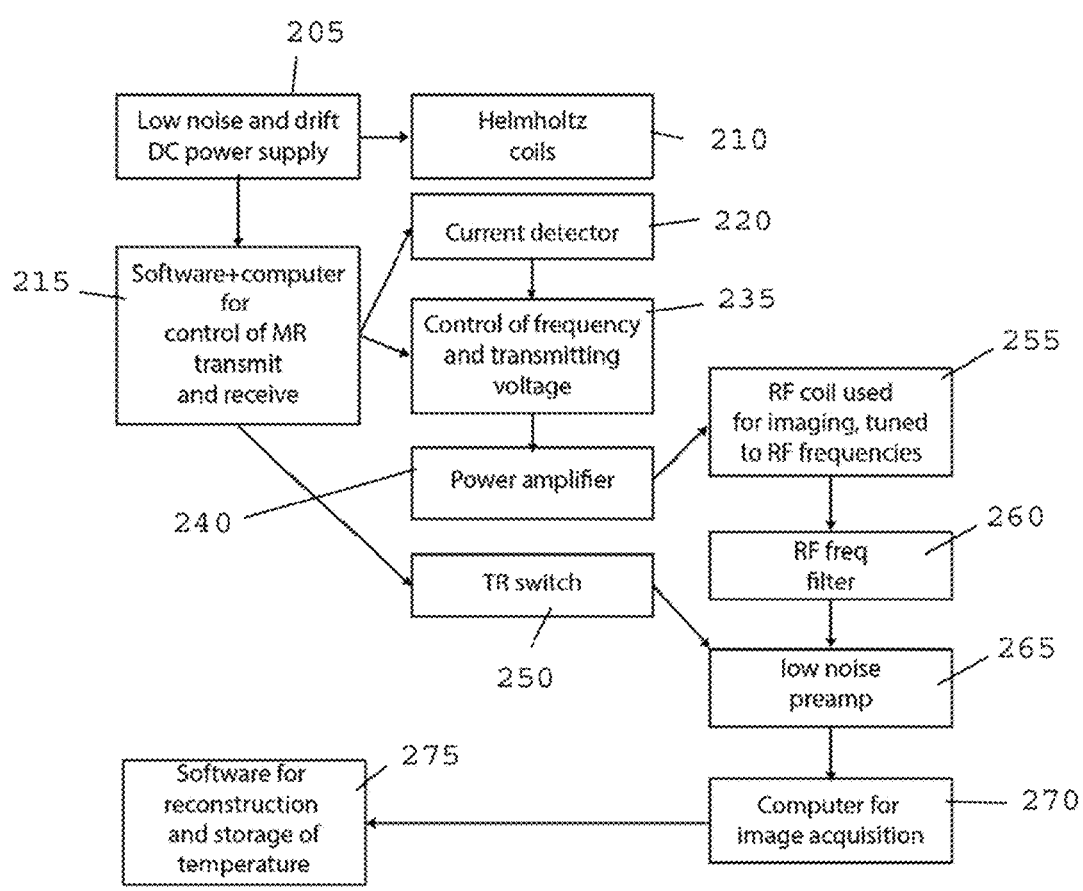
FIG. 2 is a block diagram of a representative MR thermal measurement system provided in a heating apparatus according to an exemplary embodiment of the present disclosure.

FIG. 2 illustrates an exemplary flow diagram/system according to an exemplary embodiment of the present disclosure, where the MR temperature probing or thermal sensing, system can be connected to the microwave heating circuitry, or other radiative heating control system, for example, an oven controller. The MR thermal sensing system can also be configured to provide temperature signals. or other feedback describing a temperature or temperatures inside the object to be heated, and/or a change or difference in such temperatures.

The temperature data, or feedback, can be used by the heating circuitry or control system in order to improve heating and temperature accuracy for heating of objects such as food and other materials. For example, the exemplary MR thermal sensor and heating apparatus described herein can also be applied to thermal bonding of different materials, for polymer processing or other applications in which a temperature-dependent phase change or other thermal effect can be desired, or in which a particular temperature is desired to be maintained for a preselected time.

Referring to FIG. 2, DC power supply 205, for example, a low noise DC power supply with low drift can be used to drive Helmholtz coils or other field generator 210, generating a magnetic field inside the heating apparatus. For example, in some exemplary embodiments of the present disclosure, the field can be between about 0.01 T (e.g., 0.01 tesla) and about 1 T. Alternatively, a larger or smaller field magnitude can be generated with alternative magnetic designs, for example, up to about 5-10 T, or below about 0.01 T.

A computer system 215 executing software code stored in firmware or on a non-volatile computer-readable storage medium, according to an exemplary embodiment of the present disclosure, can be utilized to detect and measure current in the coils (e.g., using current director 220), and can calculate the corresponding magnetic field and center frequency needed for excitation of MR effects inside the sample or object to be heated. A series of RF pulses can also be applied via one or more RF amplifiers 240, one or more coils (e.g., RF or MR coils 255), and through an RF frequency filter 260, in order to calculate and control a reference voltage or current level used needed to excite or induce MR effects in the object (e.g., block 235).

The signal can be fed or otherwise provided into a low noise preamp 265 before being used for reconstruction. At certain exemplary intervals (e.g., every few seconds, or at other time intervals) an image of the object can be acquired (e.g., using computer 270), for example during a heating process. Software 275 can configure a computer to cause or be used for reconstruction and storage of the temperature information. A suitable transmit-receive or TR switch 250 can be utilized to provide for safe operation of the MR receiver and pre-amp electronics. When the TR switch can be biased, a small signal can be transmitted through the (e.g., low noise preamps) to the receivers, for example, on a shielded reconstruction processor or computer system disposed inside the microwave or other radiative heating apparatus. Such exemplary MR excitation and image acquisition can be conducted at intervals during the heating process, for example, every few seconds, as described above, or on demand from a user, for example.

Exemplary Contrast and Pulse Sequences

Food quality can depend on a multitude of chemical processes including PH, concentration of metabolites, and T1 and T2 relaxation rates. In addition to temperature information acquired using the system, method and computer-accessible medium other quantities can be measured. For example, T1 was shown to be highly correlated with temperature change. T1 relaxation has been shown to be particularly sensitive to freeze-thawing of various meat samples, exhibiting a significant decrease in T1 upon freezing, and linked to meat tenderness. Bulk T2 values of water protons can be used to determine the heat-induced changes in the structure, and moisture content of fresh chicken or beef, which had been cooked. These bulk quantities can be measured by exploitation of spin echo, inversion recovery, and other sequences commonly utilized in conventional MR systems.

The exemplary images illustrated in FIGS. 3A-3D show exemplary temperature change (see e.g., FIGS. 3A and 3B) generated by a microwave and/or radiative heating apparatus and the norm of the magnetic field flux density (see e.g., FIGS. 3C and 3D) generated in the heating apparatus. Based on the exemplary images, a sufficiently high magnetic field magnitude can be provided in order to image the sample, according to an exemplary embodiment of the present disclosure.

The exemplary images illustrated in FIGS. 4A-4C show the temperature change, frequency of spin precession, and frequency shift due to heating, respectively, at an interior slice or other region of interest within an object undergoing a heating process, for example, a water sample, a food item or another material. For example, according to an exemplary embodiment of the present disclosure, the frequency of precession can be shifted once the temperature can be changed. This shift can be traceable using exemplary MR techniques by measuring the first moment of the frequency shift. Alternatively, or in addition, if imaging gradient coils are included in the system, imaging can be conducted, and the phase difference between image acquisitions can be utilized, for example, to demonstrate or exploit a substantially linear relationship in the frequency shift with respect to the temperature change.

Figure 5:
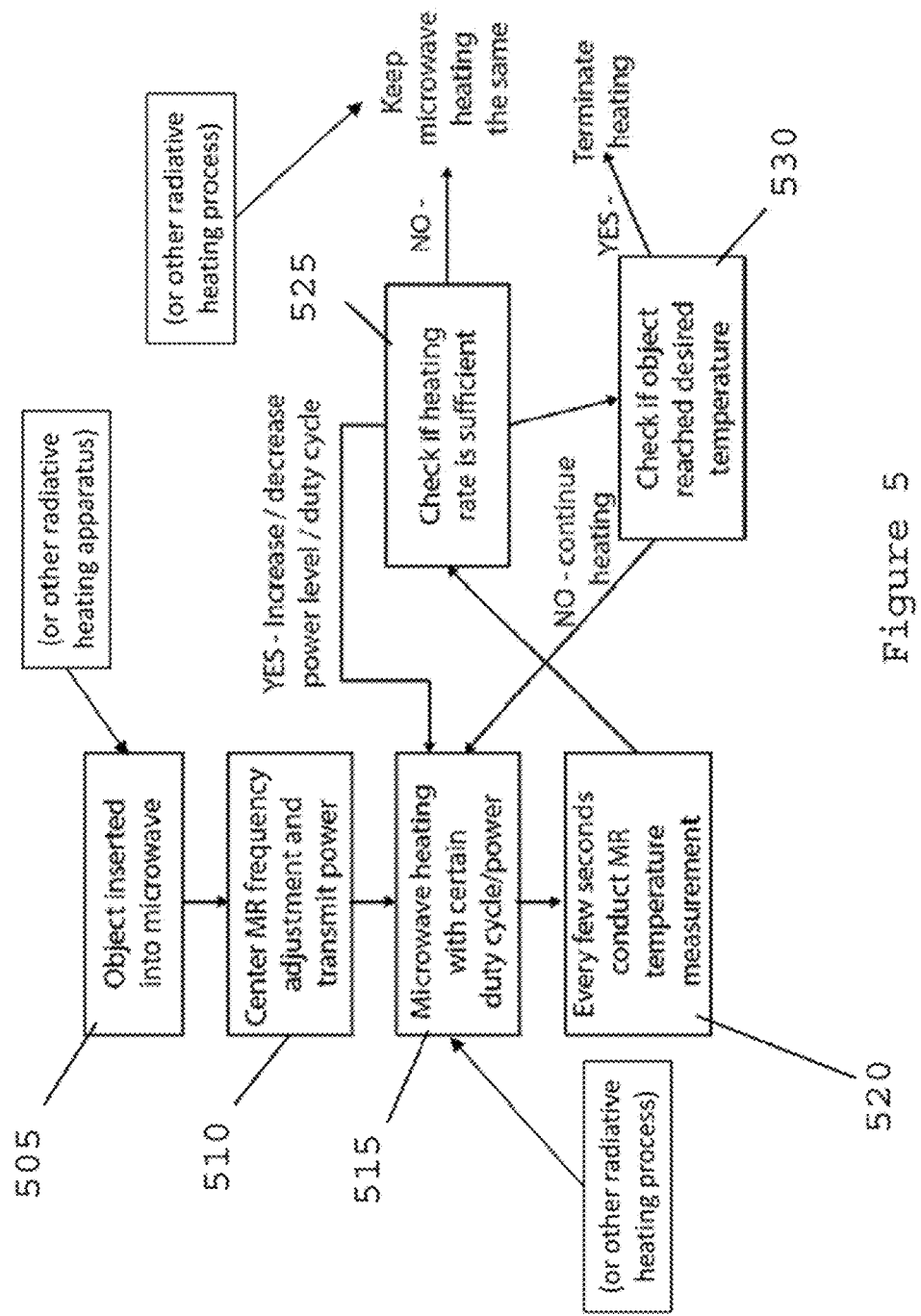
FIG. 5 is a flow diagram of an exemplary representative method for controlling radiative heating with an MR temperature measurement system according to an exemplary embodiment of the present disclosure.

FIG. 5 is an exemplary flow diagram of an exemplary method which illustrates heating panning or thermal control, according to an exemplary embodiment of the present disclosure. In this exemplary method and process, any one or more of the following steps and/or procedures can be performed, in any order or combination.

The object to be heated can be inserted into a microwave oven or other heating apparatus at procedure 505. At procedure 510, a center frequency and transmit power adjustments can be obtained using an exemplary MR system, for example an MR imaging system and/or an MR thermal measurement system coupled to the heating apparatus, as described herein. Microwave, or other heating of the object, can be performed, for example with a radiation source having a certain duty cycle and power level (e.g., selected or predetermined) at procedure 515. MR measurements of the object can be taken at intervals (e.g. every few seconds), or on demand, at procedure 520. The first moment of a first acquired MR spectrum can be mapped, or generated, for example, by a processor in communication with the exemplary MR system and the exemplary heating apparatus control system, as described herein. The moment can be defined in an analytical sense, based on an integral over the spectrum weighted by intensity. Alternatively, a higher order moment, or different averaging function, can be used. For example, an algebraic mean or peak (e.g., mode) function, or other statistical or analytic function describing the spectral distribution can be used.

The temperature of the object, or a change therein, can be determined based on the moment, or other function, of the first spectrum, and the first moment or other function can be determined for a second MR spectrum taken at a time interval after the first spectrum. The temperature of the object undergoing the heating process can be determined based on the function of the second spectrum. Alternatively, a change in the temperature of the object can be estimated or defined, based on a difference between the moments, or other functions, of the first and second spectra. At procedure 525, the heating rate of the object can be determined based on the temperature and/or the change in temperature. The heating rate can also be displayed on a display and/or monitored by the processor, for example in order control the heating process based on a desired or preselected change in temperature of the object, over a given time interval or period. At procedure 530, if the heating rate can be sufficient, or can fall within a preselected (e.g., desired) range, no action can be taken. Alternatively or in addition, if heating occurs too fast or too slow an adjustment of the power level and/or duty cycle can be made via the oven controller. For example, if the determined heating rate can be too low, or falls below a selected, or predetermined, range, the power level and/or the duty cycle of the radiation source can be increased. If the determined heating rate can be too high, or falls above the predetermined or selected range, the power level and/or duty cycle can be decreased.

A check can also be performed to determine whether the desired or preselected temperature, temperature range, T1 or T2 has been reached. If the desired or preselected temperature range can be reached, for example indicting that a given food item has a desired temperature or indicating that a material has reached a phase transition temperate (e.g., for melting or other thermodynamic transition, for a selected period of time), the microwave or other heating process (e.g., radiative) can be stopped or paused, for example, using the processor to direct the oven or heating controller. If the desired temperature or other conditions are not met, the processor and controller can direct the heating process to continue. The duty cycle and power output of the radiation source can also be adjusted based on the measured temperature, temperature change, or heating rate, as described herein.

The exemplary system, method and computer-accessible medium, according to an exemplary embodiment of the present disclosure, can include software and hardware configurations, which can be used to monitor temperature, T1 and T2 when heating objects. Since knowledge of the internal temperature of the object can be known using the exemplary system, method and computer-accessible medium, the temporal course of heating can be planned or controlled, and "heating curves" or other desired temperature functions can be defined or input (e.g., uploaded) to the processor or computer system, such that the object can be heated in a preselected or desired manner.

In addition, tracking and planning of the heating and heat planning and control may not be limited to the particular microwave frequencies or other radiation frequencies defined and described herein, and the exemplary system, method and computer-accessible medium, according to an exemplary embodiment of the present disclosure, can be employed in combination with other heat generation devices. Furthermore, other magnetic field generating geometries can be used, for example, using a number of solenoid coils, permanent magnets or other field generating devices, as configured to generate, increase or decrease the magnetic field within the heating apparatus, cavity or other volume of interest.

Figure 6:
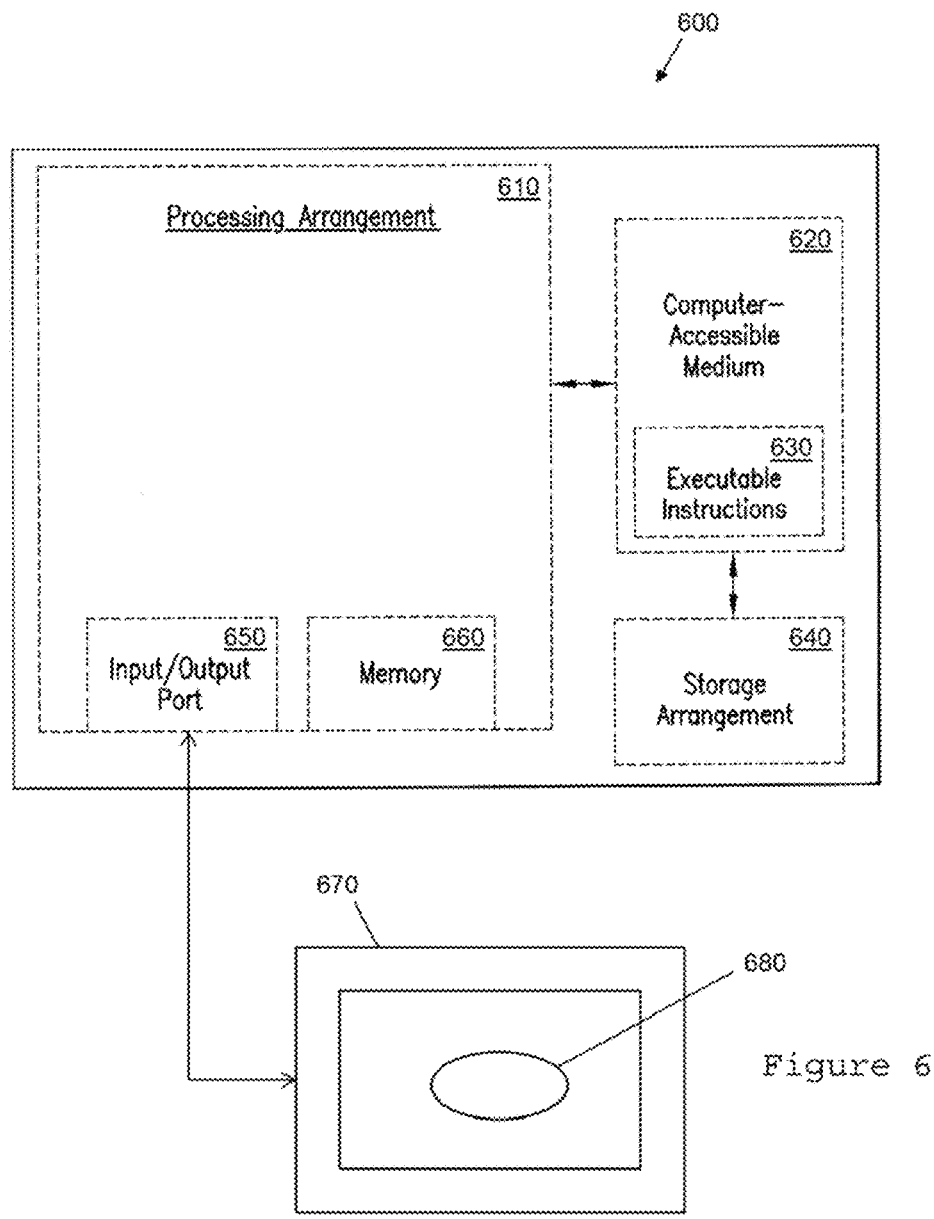
FIG. 6 is an illustration of an exemplary block diagram of an exemplary system in accordance with certain exemplary embodiments of the present disclosure.

FIG. 6 shows a representative block diagram illustrating an exemplary embodiment of a system 600 according to the present disclosure. For example, any exemplary method or procedure in accordance with the present disclosure described herein can be performed by a processing arrangement 610 and/or a computing arrangement 610. Such processing/computing arrangement 610 can be, for example, entirely or a part of, or include, but not limited to, a computer/processor that can include, for example, one or more microprocessors, and use instructions stored on a computer-accessible medium (e.g., RAM, ROM, hard drive, or other storage device).

As shown in FIG. 6, for example, a computer-accessible medium 620 (e.g., as described herein, a storage device such as a hard disk, floppy disk, memory stick, CD-ROM, RAM, ROM, etc., or a collection thereof) can be provided (e.g., in communication with the processing arrangement 610. The computer-accessible medium 620 can be a non-transitory computer readable storage medium, and can contain executable instructions 630 thereon, wherein the instructions can be executable on a computer processor or other processing arrangement 610 to perform any of the exemplary methods and processes described herein. In addition, or alternatively, a storage arrangement 640 can be provided separately from the computer-accessible medium 620, which can provide the instructions to the processing arrangement 610 so as to configure the processing arrangement to execute certain exemplary procedures, processes and methods, as described herein, for example.

Further, the exemplary processing arrangement 610 can be provided with, or can include an input/output arrangement 650, which can include, for example, a wired network, a wireless network, the internet, an intranet, a data collection probe, a sensor, etc. The input/output arrangement 650 can be configured to couple computer system 600 in communication with an apparatus 670 (e.g., a heating apparatus, an RF or IR radiation system, or an MR imaging system), configured to expose an object 680 (e.g., a body) to RF or IR radiation for heating or other purposes, as described herein. In additional examples and embodiments, apparatus 670 can take the form of a different RF system, for example an open-cavity magnetic resonance imaging system, in which object 680 can be exposed to a magnetic field and RF radiation for imaging purposes and in which heating occurs due to absorption of the RF imaging field.

As shown in FIG. 6, the exemplary processing arrangement 610 (e.g., a computing arrangement) can further be provided with and/or include exemplary memory 660, which can be, for example, cache, RAM, ROM, flash memory, etc. Further, the exemplary processing arrangement 610 can be in communication with an exemplary display arrangement which, according to certain exemplary embodiments of the present disclosure, can be a touch-screen configured for inputting information to the processing arrangement, in addition to outputting information from the processing arrangement, for example. Further, the exemplary display and/or storage arrangement 640 can be used to display and/or store data in a user-accessible format and/or user-readable format. The exemplary processing/computing arrangement 610 shown in FIG. 6 can execute the exemplary procedures described herein, as well as those shown in the drawings.

Exemplary methods and systems for measuring the RF energy deposited into a phantom or, other body, according to exemplary embodiments of the present disclosure are described herein, using, for example, the frequency distributions observed from single or isolated signal pulses, rather than by monitoring power. For example, two or more FID response signals can be acquired with a selected acquisition period on the order of a few seconds each, either before or after RF energy can be delivered to the phantom target or subject patient.

The exemplary FID signals can be processed by a Fourier transform, or other technique, to produce spectral data, (e.g. signal intensity as a function of frequency). A first moment, or other averaging function, can be calculated or otherwise determined for each FID signal, with respect to frequency. According to an exemplary embodiment of the present disclosure, the difference between the first moments of successive FID signals can correspond to an average temperature change (e.g., $\Delta T$), which can depend on the total energy deposited in the target, in the exposure time between the first and second FID measurements (e.g., the integral of the power deposition or dose over time).

Exemplary results can be determined in a similar manner for both phantom targets and in-vivo subjects, or other bodies. For example, the rate of temperature change can be estimated of or determined according to, for example:

$$\rho C \frac{dT}{dt} = \nabla \cdot (k \nabla T) + [\rho_{blood} w c_{blood}(T - T_{core})] + Q_m + SAR\rho, \quad (1)$$

where $\rho$, C, and k can be the tissue density (e.g., in kg/m$^3$), heat capacity (e.g., J/kgK or J/kg/C), and thermal conductivity (e.g., in W/m/K or W/m/C), respectively.

The first term in the exemplary Equation 1 can depend upon the temperature gradient and tissue density, and the exemplary second (e.g., perfusion) term can depend upon difference between local temperature T and core temperature $T_{core}$, multiplied by the blood density $\rho_{blood}$, volumetric flow rate w and specific heat capacity $c_{blood}$. The third term $Q_m$ can be the heat generated from metabolic processes, for example, as determined over an exposure time between the first and second FID acquisitions.

The last exemplary term in Equation 1 can include the specific absorption rate ("SAR") (e.g., in W/kg), which can be a driving force or factor in determining the temperature rise. The specific absorption rate can be defined as, for example:

$$SAR = \frac{\sigma |E|^2}{2\rho},$$

where $|E|^2$ can be the square magnitude, or square modulus, of the induced electric field strength $|E|$ (e.g., in V/m), and $\sigma$ can be the electrical conductivity (e.g., in Siemens per meter or S/m).

When the heating time or duration of exposure can be relatively short, Equation 1 can be simplified to express the SAR as, for example:

$$SAR = C \frac{\Delta T}{\Delta t}, \quad (2)$$

where $\Delta t$ can be the RF heating time interval, and $\Delta T$ can be the change in local temperature T, measured before and after RF energy deposition.

In exemplary MR applications, ΔT can be measured or monitored using a proton resonance frequency ("PRF") shift method (see, e.g., Reference 23), which relates (e.g., linearly) the temperature change ΔT to the frequency of nuclear precession. As a result, the first moment of the absolute value of the FID signal spectrum can be used to quantify or estimate the average temperature change ΔT, as determined before and after energy can be deposited in the target body by the RF coil. Thus, for example:

$$\Delta T_{avg} = \frac{1}{\alpha \cdot \omega} \cdot \left[ \frac{\int_{-\frac{BW}{2}}^{\frac{BW}{2}} f(x)_{FID1} \cdot x \cdot dx}{\int_{-\frac{BW}{2}}^{\frac{BW}{2}} f(x)_{FID1} \cdot dx} - \frac{\int_{-\frac{BW}{2}}^{\frac{BW}{2}} f(x)_{FID2} \cdot x \cdot dx}{\int_{-\frac{BW}{2}}^{\frac{BW}{2}} f(x)_{FID2} \cdot dx} \right]. \quad (3)$$

The subscripts FID1 and FID2 can represent free induction decay acquisitions before and after SAR exposure, respectively, and function $f(x)$ can represent the signal amplitude of the corresponding spectrum at each frequency point x. The proton frequency shift coefficient α can typically be about 0.01 PPM/K (e.g., in parts per million per kelvin or degree Celsius) (see, e.g., Reference 32), which can be multiplied by the Larmor frequency ω. The integrals can be performed over the bandwidth interval ±BW/2, where BW can be the bandwidth of the spectrum.

Equation 3 can be applied when the thermal dose can be applied for a short duration of time, and the effect of temperature on the PRF can be larger than that due to other (e.g., non-thermal) effects such as $B_0$ drift. Once the average temperature change ΔT can be measured via FID acquisitions FID1 and FID2, the thermal dose can be estimated or calculated based on, for example:

$$SAR = C_{avg} \frac{\Delta T_{avg}}{\Delta t},$$

where $C_{avg}$ can be the average heat capacity of the target, and $\Delta T_{avg}$ can be the corresponding average temperature change, as defined over a particular body, sample or region of interest ("ROI").

Exemplary Utilization of Small Reference Phantoms

Mapping of absolute temperature change can be highly desirable when mapping temperature of objects being heated. Referenceless thermometry can be used for these exemplary applications. However, given spectral blurring, the application of Referenceless thermometry can be difficult. As a result, it can be highly desirable to introduce a small phantom that can be placed inside the hardware apparatus. The phantom can exhibit no variation in frequency as result of heating, or a clearly defined frequency shift with temperature, where the difference between the frequencies of the phantom and the object being heated can provide absolute temperature information of the object.

Exemplary Methods

For verification of the exemplary system, method and computer-accessible medium, a gelatin phantom was used to emulate the electrical properties of human tissue by combining about 500 ml of water with about 115.4 g of gelatin, about 1 g of salt (e.g., NaCl), and about 0.5 g of benzoic acid (e.g., $C_7H_6O_2$). The electrical conductivity and relative permittivity of the phantom target were about 1 S/m and about 71, respectively, as measured using, for example, a dielectric probe or sensor (e.g., an Agilent 85070E dielectric probe kit, available from Agilent Technologies of Santa Clara, Calif., or another suitable device).

Figures 7A, 7B:
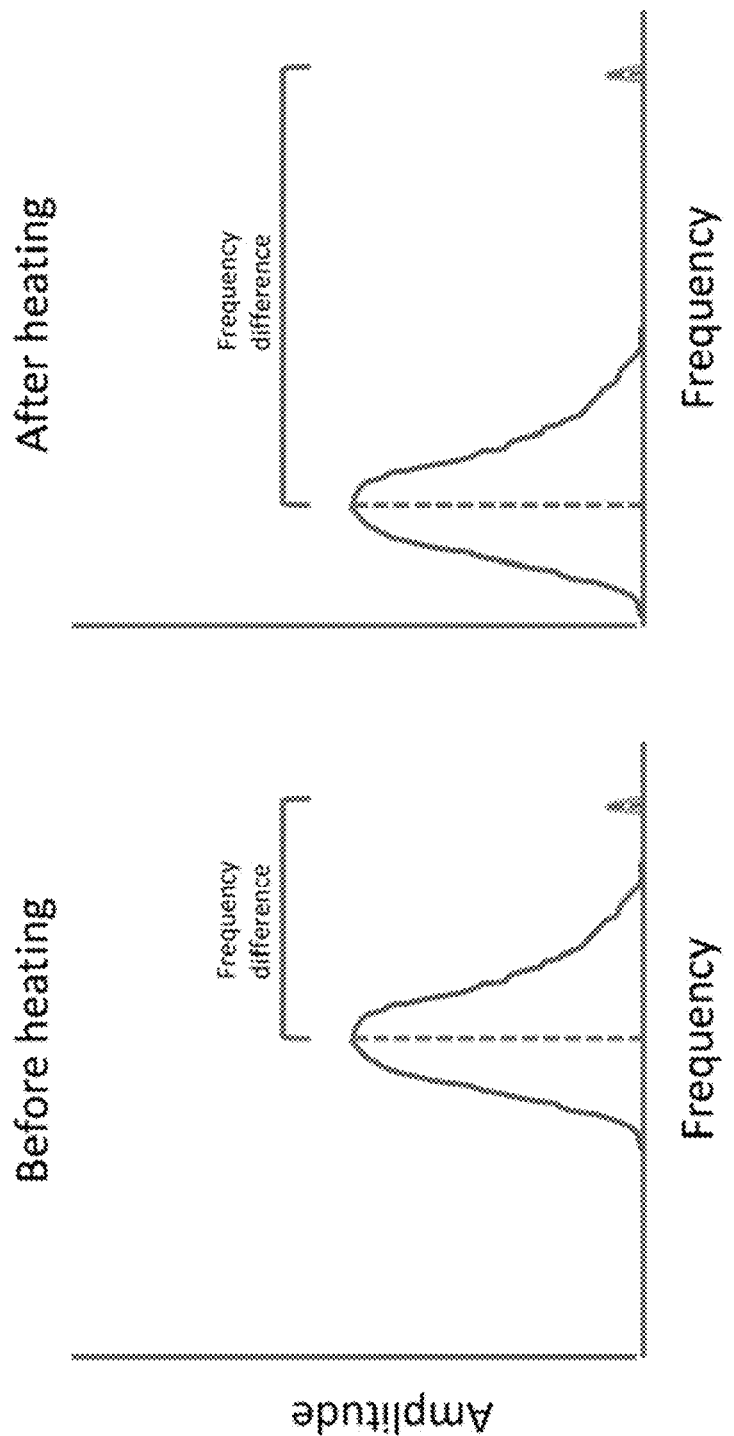
FIG. 7A is a plot illustrating the frequency difference for an exemplary reference phantom before heating according to an exemplary embodiment of the present disclosure.
FIG. 7B is a plot illustrating the frequency difference for an exemplary reference phantom after heating according to an exemplary embodiment of the present disclosure.

The gelatin mixture, or gel, was placed inside a bottle measuring about 7 cm in diameter and about 16.5 cm in height, with thermal properties measured using a thermal property sensor or probe (e.g., a KD2 Pro thermal properties analyzer, available from Decagon Devices of Pullman, Wash., or another suitable device). Based on these measurements, the thermal diffusivity, thermal conductivity, heat capacity and density of the phantom target were about 0.146 $m^2/s$, about 0.572 W/m/K, about 3460 J/kg/K and about 1064 $kg/m^3$, respectively. (See e.g., FIGS. 7A and 7B)

Figure 8A:
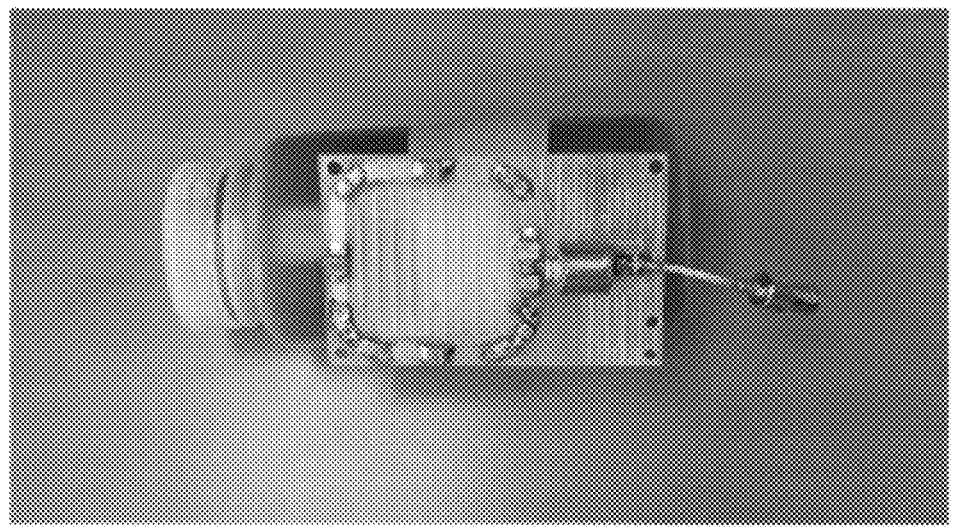
FIG. 8A is a photograph of a top view of a loop coil for RF heating, coupled to a phantom target, according to an exemplary embodiment of the present disclosure.

An exemplary loop coil configured for heating was placed on top of the phantom (see e.g., FIG. 8A), inside a 28 element QED knee coil array (e.g., as available from Quality Electrodynamics of Mayfield Village, Ohio, or another suitable device). The loop coil was tuned to a frequency of about 275 MHz, and placed inside the RF coil in a 7 T MRI system (e.g., as available from Siemens Medical Solutions or Erlangen, Germany, or using another suitable MR imaging system).

A series of ten FID signals were acquired about thirty seconds apart, after which the loop coil was connected to an RF amplifier delivering about 74.7 W of continuous power for about 1 minute (e.g., a Kalmus LA200UELP or similar amplifier available from AR Modular RF—formerly AR Kalmus—of Bothell, Wash., or another suitable device). After about one minute of heating the sample, nine more FID signals were acquired, for example over an acquisition period of about 2 seconds each, with flip angle ("FA")=90°, matrix size=4096, and bandwidth BW of about 2000 Hz.

Before and after the heating process, a 2D interleaved spoiled gradient echo ("GRE") image was acquired in order to validate the frequency shifts quantified using the FID signals, for example with echo time TE of about 15 ms, repetition time TR of about 208 ms, volume characteristics 2.5×2.5×5 $mm^3$, flip angle=25°, and matrix size 64×64×12, with an acquisition time of about 13.3 s. The first moment of the spectra corresponding to the FID signals was then calculated, and a ΔT map was reconstructed from the GRE images.

Figure 8B:
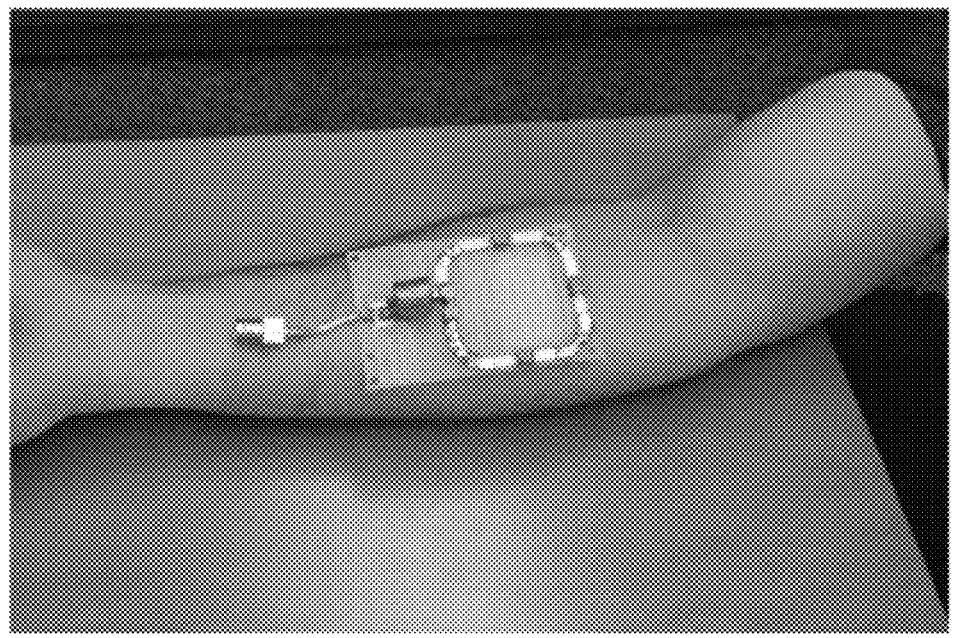
FIG. 8B is a photograph of a top view of the loop coil shown in FIG. 8A positioned on the forearm of a subject according to an exemplary embodiment of the present disclosure.

Exemplary In Vivo Analysis:

For an exemplary in vivo analysis, a loop coil was placed on the forearm of a subject (see e.g., FIG. 8B), inside a single channel birdcage coil in the 7 T scanner used for phantom testing, as described above. A single FID was acquired with the same parameters as above, followed by a GRE with TE of about 10 ms, TR of about 290 ms, volume 2.5×2.5×5 $mm^3$, FA=25°, matrix size 64×64×16 and an acquisition time of about 18.6 s. The loop coil was then driven with about 36.3 W of power for about 1 minute, after which second FID and GRE were acquired, with the same parameters. The difference in the first moments of the two FID signals was then calculated, and a ΔT measurement or mapping was reconstructed using the PRF method.

Exemplary Results

Figure 9A:
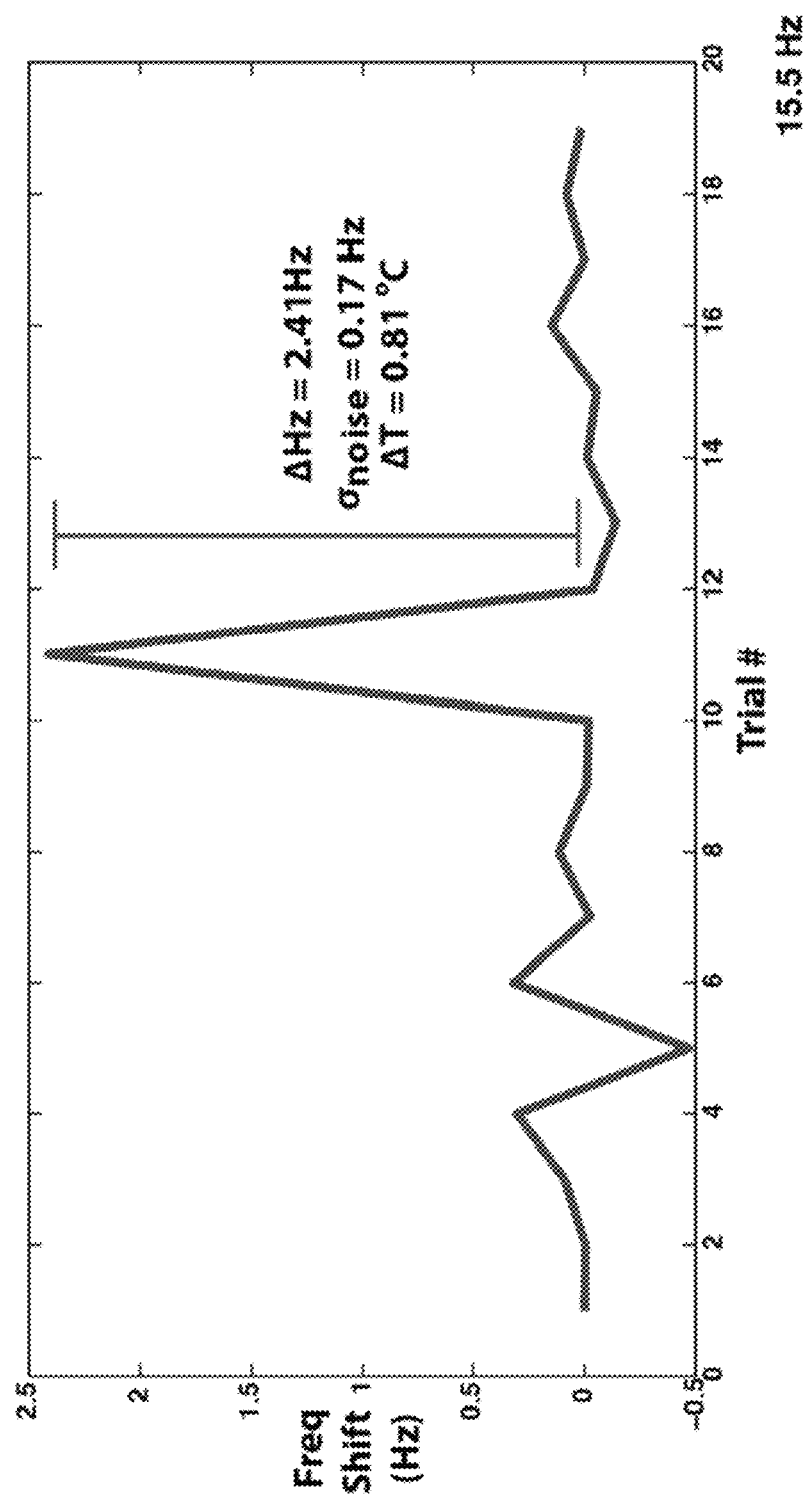
FIG. 9A is a plot of frequency shift versus trial number, illustrating the difference in frequency, or frequency shift, due to heating of the phantom, according to an exemplary embodiment of the present disclosure.
Figure 9D:
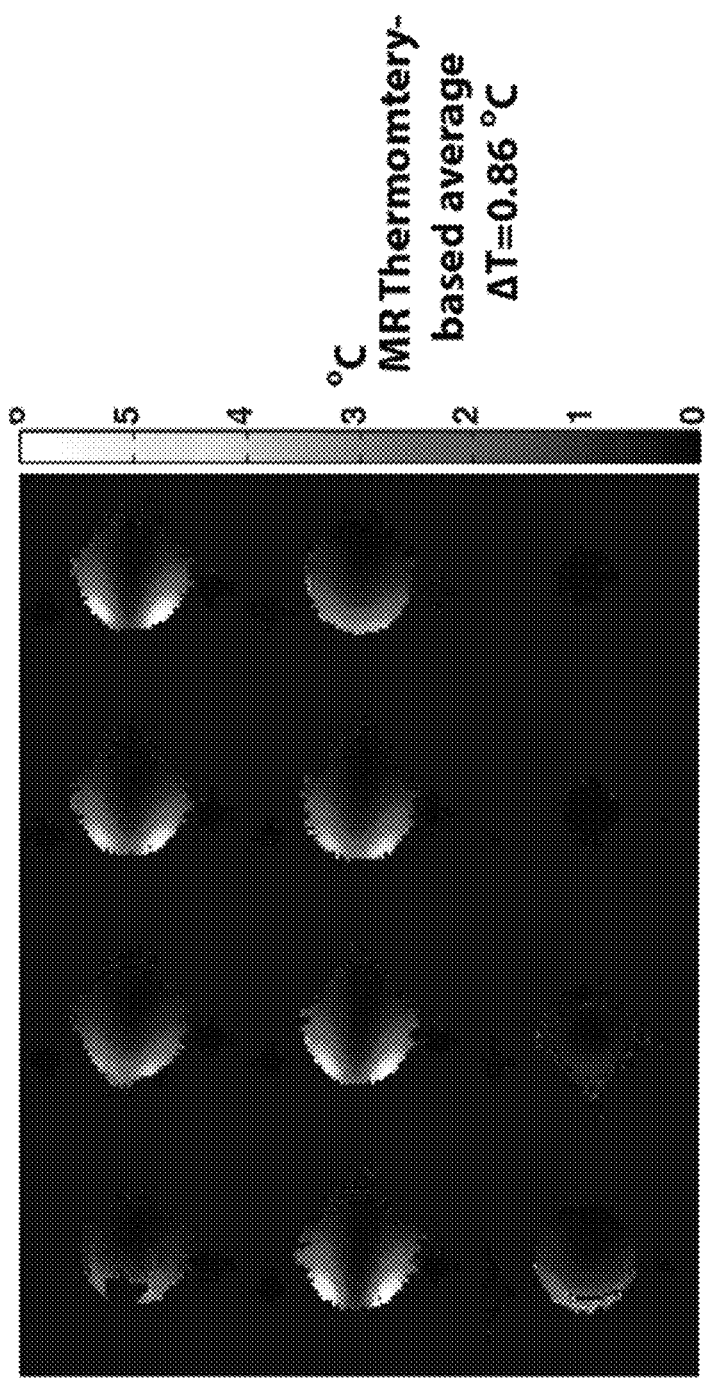
FIG. 9D is a series of exemplary MR thermometry images of the exemplary phantom according to an exemplary embodiment of the present disclosure.

FIGS. 9A-9D show graphs of exemplary results of the phantom experiments, including the average temperature difference ΔT reconstructed by subtracting the first moment of the FID spectrum before heating (e.g., element 905) and after heating (e.g., element 910). (See e.g., FIG. 9A). The difference between the FID and volume-averaged MR thermometry based measurement was about 6%, while the standard deviation of the difference in the first moments was 0.17 Hz, when no RF heating was applied. Such exemplary result can be substantially smaller than the difference between the first moments before and after heating, which was about 2.41 Hz. The change in the FID first moment as a result of RF power deposition is shown in FIGS. 9B and 9C, with an FID based average temperature change $\Delta T=0.81°$ C. This compares to $\Delta T=0.86°$ C. for the MR thermometry based average, as shown in FIG. 9D.

FIGS. 10A-10C show images of exemplary results of the exemplary in vivo analysis, again comparing MR thermometry and FID based results for pre heating (e.g., element 1005) and post heating (e.g., element 1010). For example, FIGS. 10A and 10B show that the FID-based measurement can yield an average temperature change of $\Delta T=0.37°$ C., as compared to an MR thermometry based result of $\Delta T=0.46°$ C., for a difference in $\Delta T$ of about 20%. (See e.g., FIG. 10C).

The exemplary system/method according to an exemplary embodiment of the present disclosure can monitor thermal changes in water-based objects. Current state-of-the-art scanners provide homogeneous magnetic fields with stable main magnetic fields. The exemplary system/method according to an exemplary embodiment of the present disclosure can utilize a low cost, permanent or resistive magnet design that does not have to be homogeneous. These exemplary magnets can be designed to be inhomogeneous to reduce the cost of the magnet, and can relate to microwave's, or other heating device's, geometrical constraints. Conducting MR thermometry experiments at inhomogeneous fields can be challenging. Therefore, the exemplary system/method according to an exemplary embodiment of the present disclosure can use a combination of hardware and software solutions to facilitate MR thermometry experiments.

Exemplary Main Magnetic Field Drift and Spatial Compensation System

Imaging at inhomogeneous fields can utilize correction of the main magnetic field drift, as well as the spatial distribution of the B0 experiments. This can be particularly important when conducting MR thermometry experiments using the PRF shift method. In order to perform the experiments, certain exemplary solutions can be used. One exemplary solution can be or include a feedback system including hall-effect sensors that can be connected to a FPGA that, in real-time, can provide the magnetic field strength at different locations of the field-of-view ("FOV"). Before each RF pulse, a microprocessor, an ASIC or a FPGA can read the voltage at the terminals of the hall-effect sensor. The voltage can be proportional to the magnetic field strength at the position of the sensor. Readings can take place at different locations, and a three-dimensional interpolation of the main magnetic field can take place close to real time. The information from the hall-effect sensors can then be used to adjust the frequency of the subsequent RF pulses generated by the exemplary system. Another exemplary solution for facilitating a proper calibration of the exemplary system can use NMR probes placed at different locations. These probes can contain chemicals that can be sensitive to temperature, such as ethylene glycol, DOTMA- and others. By design, these NMR probes can have a short T1, such that full relaxation can occur between the pulses, and the signal-to-noise ratio may not be compromised. Similarly, NMR probes resonating at frequencies that may not be the proton resonance frequency can be used. If non-proton NMR probes can be used, excitation at different frequencies can be needed, with the advantage of the two NRM signals (e.g., proton and non-proton) being decoupled and excitation can be performed in an interleaved fashion. Signals from the NMR probes can be acquired using transmit/receive solenoid coils that can be designed to be very small and hidden within the case of the exemplary device. Upon signal reception, a microprocessor/ASIC/FPGA can conduct a Fourier transform on the signal, and information from all the probes can be used for a 3D interpolation of the magnetic field.

Exemplary Equipment Shielding

System design in a microwave environment can pose a challenge in terms of the interference (e.g., heating) of the MRI electronics from the microwave energy. In microwaves, for example, the power levels can be greater than about 60 dBm. This large amount of energy can couple to the MRI electronics, can cause heating and can potentially damage the electronics. Furthermore, the NMR signals can be smaller than about 150 dBm. Thus, it can be beneficial to minimize or otherwise reduce coupling and to shield the MM equipment from the microwave heating apparatus. As a result, a two-chamber solution can be used where the inner chamber can be used to contain the microwave energy using conventional physical RF filters. The exemplary outer layer of the shielding can be a low pass faraday shield that can be used to minimize external interference with the NMR signal. The magnet coils and the transmit-receive RF coils can be contained between the outer shield and the inner microwave shield. The magnetic field probes in the form of hall-effect sensors, or NMR sensors, can be placed between the inner and outer shields, providing real time feedback information regarding the three-dimensional distribution of the magnetic field.

FIG. 11A shows a diagram of the structure/design of an outer shield 1105 and an inner shield 1110 used in or with the exemplary system/method according to an exemplary embodiment of the present disclosure. FIG. 11B shows an exemplary schematic/flow diagram of the exemplary system/method according to an exemplary embodiment of the present disclosure. For example, as shown in FIG. 11B, a hall affect sensor 1120 be connected to a filter 1120 (e.g., a low pass filter), prior to analog to digital conversion ("ADC") 1125. Alternatively, or in addition, a NMR sensor can be connected to a transmit/receive switch 1130, which can be connected to a filter 1135 (e.g., a band pass filter), prior to ADC 1125. Digital signals from the ADC 1125 can be streamed to a computer 1140 (e.g., microprocessor, ASIC, FPGA, etc.) to compute the 3D main magnetic field map 1145. RF pulse adjustments 1150 can be performed on the 3D main magnetic field map 1145, including center frequency changes 1160 and spatial/frequency selection 115. This information can be used to adjust the exemplary system and/or for thermal mapping 1165.

Exemplary System Adjustment

Figure 12:
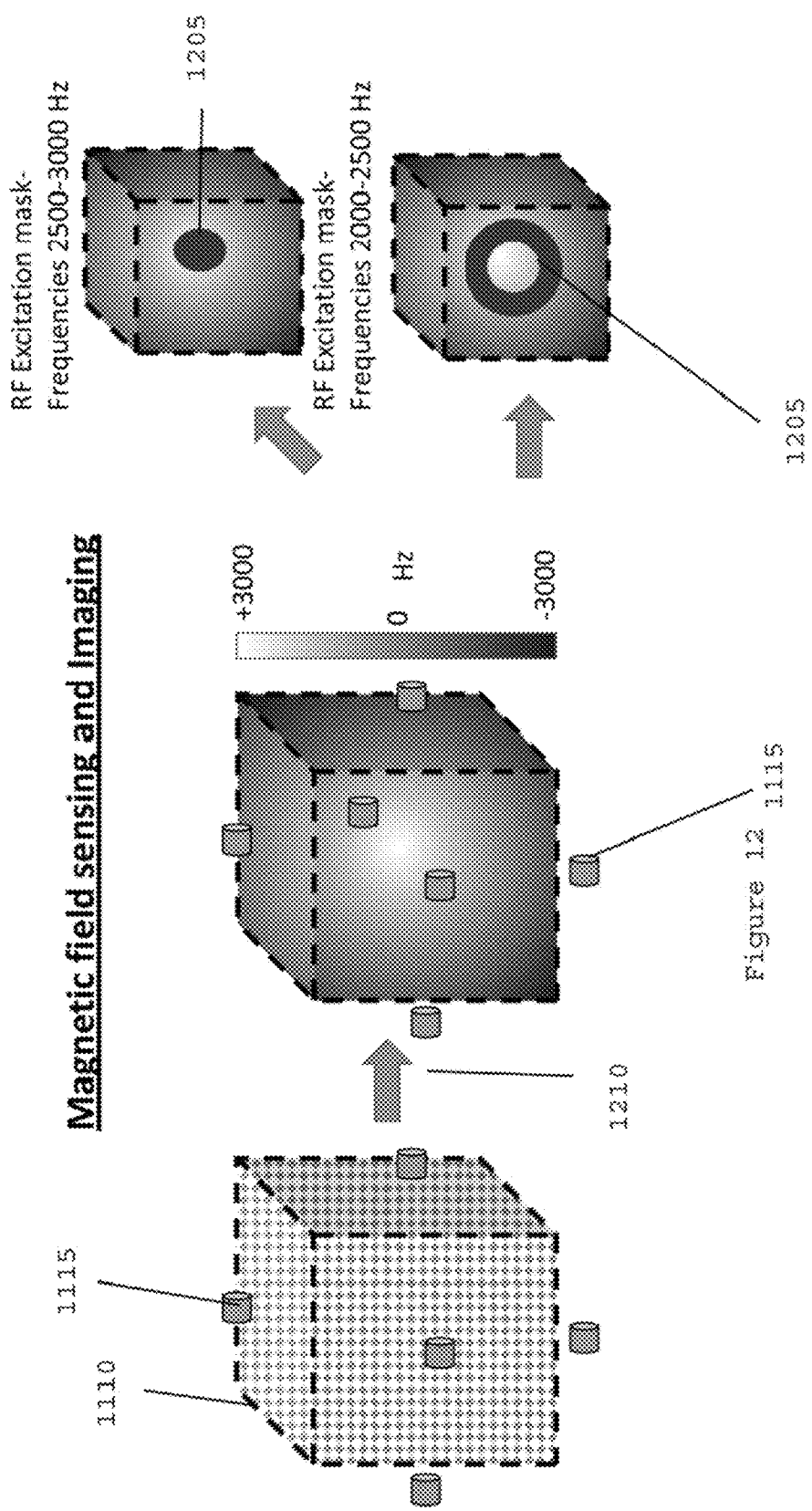
FIG. 12 is a diagram illustrating how a frequency selective pulse can be used to excite the center of the sample according to an exemplary embodiment of the present disclosure.

Information can be used by the exemplary system/method to control the RF pulses generated by the thermal scanner. Magnet solutions that utilize resistive or permanent magnets, can be sensitive to temperature changes. These temperature changes can result in a frequency offset that can introduce errors in the thermal mapping. Therefore, information from the hall effect sensors and/or NMR sensors can be used to adjust the center frequency of the RF pulses. The exemplary mapping of the magnetic field can also be used to create spatial-frequency selective pulses that can excite only a section of the sample. FIG. 12 shows an exemplary diagram illustrating how an exemplary frequency selective pulse can be used to excite the center of the sample 1205, according to an exemplary embodiment of the present disclosure. For example, as shown therein, a frequency selective pulse 1210 can be used to excite the center of the sample 1205 (e.g., which typically cannot be done in conventional clinical MRI scans).

The exemplary main magnetic field mapping can be used in conventional FID acquisitions as well as spin-echo experiments that can be more robust against field inhomogeneity. Similarly, for typical temperature measurements, two or more FIDs can be beneficial. Further, using the exemplary magnetic field sensor system, the central moment of the magnetic field can be computed and therefore, only one FID acquisition may be needed.

Exemplary Image Visualization

The exemplary information from the NMR/MRI thermal imaging according to an exemplary embodiment of the present disclosure can be combined with optical imaging. Optical imaging can be used to reconstruct the object in three dimensions, while the field probe information can be used to provide localized heating information inside the object. Infrared imaging can be used to further improve the accuracy of the exemplary system/method.

Exemplary Conclusion

Exemplary method, system and computer-readable medium for measuring average power deposition can be provided, according to the exemplary embodiments of the present disclose, with exemplary results validated in phantom targets and in vivo testing. The exemplary use of FID acquisition to quantify thermal dose can facilitate one or more measurements of small $\Delta T$, for example, insomuch as the frequency shift caused by thermal dosing (e.g., RF heating) can generally be higher than the shift due to the innate $B_0$ changes that can occur during scanning.

For example, where the thermal dose can be applied over a short duration of time, heat diffusion can be small, and Equation 2 described above can remain valid for expressing the SAR. The exemplary system, method and computer-accessible medium, according to an exemplary embodiment of the present disclosure, can also facilitate a measurement of the global RF energy coupling into a patient, or other subject, in which the signals can arise substantially or predominantly from resonant water interactions, and when the receive coil can have relatively uniform distribution over the heated region.

The foregoing merely illustrates the principles of the present disclosure. Various modifications and alterations to the described embodiments will be apparent to those skilled in the art in view of the teachings herein. It will thus be appreciated that those skilled in the art will be able to devise numerous systems, arrangements, and methods which, although not explicitly shown or described herein, embody the principles of the present disclosure and are thus within the spirit and scope of the present disclosure. In addition, all publications and references referred to herein are hereby incorporated herein by reference in their entireties. It should be understood that the exemplary procedures described herein can be stored on any computer-accessible medium, including, for example, a hard drive, RAM, ROM, removable discs, CD-ROM, memory sticks, etc., included in, for example, a stationary, mobile, cloud or virtual type of system, and executed by, for example, a processing arrangement which can be or include one or more hardware processors, including, for example, a microprocessor, mini, macro, mainframe, etc.

EXEMPLARY REFERENCES

The following references are hereby incorporated by reference in their entireties:

[1] Engineers' Handbook of Industrial Microwave Heating (Power & Energy Series) by R. J. Meredith (Dec. 1, 1998).

[2] Rieke, V. & Butts Pauly, K. MR thermometry. J. Magn. Reson. Imaging 27, 376-390, doi:10.1002/jmri.21265 (2008).

[3] Zhu, Y., et al. (2012), System and SAR characterization in parallel RF transmission. Magn Reson Med, 67: 1367-1378.

[4] C. M. Collins et al., JMRI, vol. 19, pp. 450-6, May 2004.

[5] Pearce, K. L., Rosenvold, K., Andersen, H. J., & Hopkins, D. L. (2011). Water distribution and mobility in meat during the conversion of muscle to meat and ageing and the impacts on fresh meat quality attributes—A review. Meat Science, 89(2), 111-124.

[6] Jean-Louis Damez, Sylvie Clerjon. Quantifying and predicting meat and meat products quality attributes using electromagnetic waves: An overview. INRA, UR370 Qualite des Produits Animaux, F-63122 Saint Genes Champanelle, France. Meat Science. 2013.

[7] Luca Venturi .NMR Study of Meat as Related to its Structural Organisation. Doctorate thesis. universita' di bologna 2006.

What is claimed is:

1. A non-transitory computer-accessible medium having stored thereon computer-executable instructions for determining at least one temperature change in at least one structure, wherein, when a computer arrangement executes the instructions, the computer arrangement is configured to perform procedures comprising:
receiving information related to first and second free induction decay signals provided from the at least one structure, wherein each of the first and second free induction signals is based on a radio frequency (RF) energy transmitted to the at least one structure; and
determining the at least one temperature change in the at least one structure based on the information.

2. The computer-accessible medium of claim 1, wherein the computer arrangement is further configured to expose the at least one structure to the RF energy in a magnetic field, and select a frequency of the RF energy for resonant spin interactions with the at least one structure based on a magnitude of the magnetic field.

3. The computer-accessible medium of claim 2, wherein the structure includes at least one of at least one anatomical structure, at least one body, at least one patient or at least one phantom.

4. The computer-accessible medium of claim 1, wherein the computer arrangement is further configured to estimate a thermal dose applied to the at least one structure based on the at least one temperature change.

5. The computer-accessible medium of claim 4, wherein the computer arrangement is further configured to control at least one of a magnitude of a magnetic field or a magnitude of the RF energy to which the at least one structure is exposed based on the thermal dose.

6. The computer-accessible medium of claim 4, wherein the thermal dose includes a specific absorption rate (SAR) of the RF energy by the at least one structure.

7. The computer-accessible medium of claim 1, wherein the computer arrangement is further configured to:
receive further RF energy from the at least one structure that is based on the RF energy; and
generate an image of an interior of the at least one structure based on the further RF energy.

8. The computer-accessible medium of claim 7, wherein the image includes a map of the at least one temperature change in an interior of the at least one structure.

9. The computer-accessible medium of claim 7, wherein the image includes a map of a specific absorption rate in an interior of the at least one structure.

10. The computer-accessible medium of claim 1, wherein the computer arrangement is further configured to estimate a specific absorption rate (SAR) of the RF energy based on the at least one temperature change.

11. The computer-accessible medium of claim 10, wherein the computer arrangement is further configured to control a magnitude of a magnetic field to which the at least one structure is exposed based on the SAR.

12. The computer-accessible medium of claim 10, wherein the computer arrangement is further configured to control a magnitude of the RF energy based on the SAR.

13. The computer-accessible medium of claim 10, wherein the computer arrangement is further configured to terminate exposure of the at least one structure to the RF energy based on the SAR.

14. The computer-accessible medium of claim 10, wherein the computer arrangement is further configured to estimate the SAR by scaling the at least one temperature change by a specific heat of the at least one structure divided by an exposure time of the at least one structure to the RF energy.

15. The computer-accessible medium of claim 1, wherein the computer arrangement is further configured to generate further information related to first and second RF frequency spectra that characterize the first and second free induction decay signals, respectively.

16. The computer-accessible medium of claim 15, wherein the computer arrangement is further configured to generate a respective first moment of each of the first and second RF frequency spectra.

17. The computer-accessible medium of claim 16, wherein the computer arrangement is further configured to determine the at least one temperature change at least one of (i) based on a difference between the first moment of the first RF spectrum and the first moment of the second RF spectrum, (ii) by scaling the temperature change substantially linearly by a difference between the first moment of the first RF spectra and the second moment of the second RF spectra or (iii) by dividing the difference by a proton shift coefficient and a Larmor frequency characteristic of the at least one structure in a magnetic field.

18. The computer-accessible medium of claim 17, wherein the computer arrangement is further configured to correct at least one field drift.

19. The computer-accessible medium of claim 18, wherein the computer arrangement is configured to correct the at least one field drift in a inhomogeneous field.

20. The computer-accessible medium of claim 17, wherein the computer arrangement is further configured to control at least one of a magnitude of the magnetic field or a magnitude of the RF energy to which the at least one structure is exposed based on the at least one temperature change.

21. An apparatus comprising:
a radiative heating arrangement including a radiation source which is configured to generate at least one radiation for absorption by at least one object;
a magnetic resonance (MR) arrangement including at least one coil arrangement which is configured to transmit and receive radio frequency (RF) energy to and from the at least one object; and
a computer arrangement which is configured to:
receive information related to first and second free induction decay signals provided from the at least one object, wherein each of the first and second free induction signals is based on the RF energy transmitted to the at least one object; and
determine at least one temperature change in the at least one object based on the information.

22. The apparatus of claim 21, wherein the computer arrangement is further configured to determine the information based on a first moment of a MR spectrum.

23. The apparatus of claim 21, further comprising a housing, and wherein the MR arrangement is provided within the housing.

24. The apparatus of claim 21, wherein the radiative heating arrangement includes a microwave generator configured to generate a microwave radiation for absorption by the at least one object.

25. The apparatus of claim 21, wherein the at least one radiation is at least one of microwave radiation, thermal radiation or infrared radiation.

26. The apparatus of claim 21, wherein the computer arrangement is further configured to generate at least one image of the at least one object based on the received RF energy.

27. The apparatus of claim 26, wherein the at least one image represents an interior of the at least one object.

28. The apparatus of claim 27, wherein the at least one image includes a temperature map of the interior of the at least one object.

29. A system for determining at least one temperature change in at least one structure, comprising:
a computer arrangement configured to:
receive information related to first and second free induction decay signals provided from the at least one structure, wherein each of the first and second free induction signals is based on a radio frequency (RF) energy transmitted to the at least one structure; and
determine the at least one temperature change in the at least one structure based on the information.

30. A method for determining at least one temperature change in at least one structure, comprising:
receiving information related to first and second free induction decay signals provided from the at least one structure, wherein each of the first and second free induction signals is based on a radio frequency (RF) energy transmitted to the at least one structure; and
using a computer hardware arrangement, determining the at least one temperature change in the at least one structure based on the information.

* * * * *